US006823866B2

(12) United States Patent
Jafari et al.

(10) Patent No.: US 6,823,866 B2
(45) Date of Patent: Nov. 30, 2004

(54) MEDICAL VENTILATOR TRIGGERING AND CYCLING METHOD AND MECHANISM

(75) Inventors: Mehdi M. Jafari, Laguna Hills, CA (US); Gardner J. Kimm, Carlsbad, CA (US); Karrie McGuigan, San Marcos, CA (US)

(73) Assignee: Respironics, Inc., Murrysville, PA (US)

( * ) Notice: Subject to any disclaimer, the term of this patent is extended or adjusted under 35 U.S.C. 154(b) by 0 days.

(21) Appl. No.: 10/617,590

(22) Filed: Jul. 11, 2003

(65) Prior Publication Data

US 2004/0103896 A1 Jun. 3, 2004

Related U.S. Application Data

(63) Continuation of application No. 09/970,383, filed on Oct. 2, 2001, now Pat. No. 6,626,175.
(60) Provisional application No. 60/238,387, filed on Oct. 6, 2000.

(51) Int. Cl.$^7$ ............................................. A61M 16/00
(52) U.S. Cl. ............................. 128/204.21; 128/204.18
(58) Field of Search ..................... 128/200.24, 203.12, 128/204.18, 204.21, 204.23, 204.26, 204.24, 205.11, 205.23, 207.14; 600/300, 301

(56) References Cited

U.S. PATENT DOCUMENTS

| | | | |
|---|---|---|---|
| 5,390,666 A | 2/1995 | Kimm et al. | |
| 5,503,146 A | 4/1996 | Froehlich et al. | |
| 5,572,993 A | 11/1996 | Kurome et al. | |
| 5,598,838 A | 2/1997 | Servidio et al. | |
| 5,632,269 A | 5/1997 | Zdrojkowski | |
| 5,647,351 A | 7/1997 | Weismann et al. | |
| 5,794,615 A | 8/1998 | Estes | |
| 5,803,066 A | 9/1998 | Rapoport et al. | |
| 5,937,853 A | 8/1999 | Strom | |
| 5,954,051 A | 9/1999 | Heinonen et al. | |
| 6,119,686 A | 9/2000 | Somerson et al. | |
| 6,142,150 A | 11/2000 | O'Mahoney | |
| 6,289,890 B1 | 9/2001 | Bliss et al. | |
| 6,345,619 B1 | 2/2002 | Finn | |
| 6,371,113 B1 | 4/2002 | Tobia et al. | |
| 6,390,091 B1 | 5/2002 | Banner et al. | |
| 6,401,713 B1 | 6/2002 | Hill et al. | |
| 6,422,237 B1 | 7/2002 | Engel et al. | |
| 6,439,229 B1 | 8/2002 | Du et al. | |
| 6,626,175 B2 * | 9/2003 | Jafari et al. ............ | 128/204.21 |

OTHER PUBLICATIONS

Branson, Richard D., et al. "Respiratory Care Equiptment," Chapter 13 (Robert Chatburn), pp. 264, 276–278, J.B. Lippincott Co. publisher, 1995.

Pilbeam, Susan P., "Mechanical Ventilation, Physiological and Clinical Applications," Chapters 2–3, pp. 19–47, Chapters 5–6, pp. 63–122, Multi–Media Publishing, Inc., 1986.

White, Gary C. "Equipment Therory for Respiratory Care, 3rd Edition", Chapter 6, pp. 333–372, Delman Publishers, 1998.

* cited by examiner

*Primary Examiner*—Henry Bennett
*Assistant Examiner*—Teena Mitchell
(74) *Attorney, Agent, or Firm*—Michael W. Haas

(57) ABSTRACT

A medical ventilator system and method that triggers, cycles, or both based on patient effort, which is determined from cross-correlating patient flow and patient pressure. The medical ventilator is also controlled such that sensitivity to a patient initiated trigger increases as the expiratory phase of the breathing cycle progresses. The present invention also provides adaptive adjustment of cycling criteria to optimize the cycling operation.

27 Claims, 4 Drawing Sheets

MEDICAL VENTILATOR TRIGGERING AND CYCLING METHOD AND MECHANISM

CROSS-REFERENCES TO RELATED APPLICATIONS

This application claims priority under 35 U.S.C. § 120 as a Continuation of U.S. patent application Ser. No. 09/970,383 filed Oct. 2, 2001, now U.S. Pat. No. 6,626,175, which priority under 35 U.S.C. §119(e) from provisional U.S. patent application Ser. No. 60/238,387 filed Oct. 6, 2000.

BACKGROUND OF THE INVENTION

1. Field of the Invention

The present invention pertains to a medical ventilator with improved spontaneous triggering and cycling and to an improved method of triggering and cycling such a ventilator. In particular, the present invention pertains to a ventilator with one or more of the following features: (1) sensitivity to a patient initiated trigger that increases as the expiratory phase of the breathing cycle progresses, (2) adaptive adjustment of cycling criteria to optimize the cycling operation, and (3) triggering, cycling, or both based on patient effort, which is determined from cross-correlating multiple patient parameters.

2. Description of the Related Art

It is known to utilize a conventional ventilator or pressure support device to deliver a fluid, such as oxygen, air or other oxygen or breathing gas mixture, to an airway of patient to augment or substitute the patient's own ventilatory effort. It is further known to operate a conventional ventilator in a variety of modes to control the four basic operations of a ventilator, which are: 1) the trigger point, which is the transition from the expiratory to the inspiratory phase of the ventilatory cycle; 2) the inspiratory phase where the ventilator delivers the flow of breathing gas; 3) the cycle point, which is the transition from the inspiratory phase to the expiratory phase, and 4) the expiratory phase. There are four primary variables or parameters that are typically monitored and used to control how a ventilator performs one or more of these four operations. These variables are the volume, pressure, flow of fluid to or from the patient, and time.

In a typical life support situation, where there is substantially no spontaneous respiratory effort by the patient, a controlled mode of ventilation is provided, where the ventilator assumes full responsibility for ventilating the patient. In this mode of ventilation, the trigger and cycle point of the ventilator are determined based on time. In other situations, where the patient exhibits some degree of spontaneous respiratory effort, an assist mode or a support mode of ventilation is typically provided. Both of these modes of ventilation cause the ventilator to augment or assist in the patient's own respiratory efforts. In the assist mode, the determination of the ventilator trigger point is based on the action of the patient and the determination of the cycle point is determined based on time. In the support mode, both the trigger and the cycle points are patient based and not based on time. It is also known to use a combination of these two modes, referred to as an assist/control mode of ventilation. In this mode of ventilation, the ventilator triggers an inspiratory flow only if the patient fails to initiate a respiratory effort for a period of time. Thus, the trigger point is based on either a patient action or on time, if there is no patient action within a certain period of time.

In the assist, support, and assist/control modes of ventilation, it is important that the operation of the ventilator is synchronized with the patient's spontaneous respiratory effort, so that the ventilator triggers the inspiratory flow of breathing gas at or near the time the patient begins his or her inspiratory effort, and cycles to the expiratory phase of the breathing pattern at an appropriate time, preferably when the patient begins his or her expiratory phase of the breathing cycle. Conventional ventilators operating in an assist, support, or assist/control mode of ventilation typically monitor only one patient parameter, such as the pressure, flow, or volume, and use this single monitored parameter as a variable in determining when to spontaneously trigger the delivery of the inspiratory flow. Typically, the monitored parameter is compared to a threshold, and if the threshold is exceeded, the transition from expiration to inspiration (trigger) or from inspiration to expiration (cycle) is initiated. In other pressure support devices, the current value of the monitored parameter is compared to a previous value of the same parameter, so that the ventilator triggers or cycles based on the result of this comparison. U.S. Pat. No. 5,632,269 to Zdrojkowski et al. teaches this technique referred to as "shape triggering."

This one-dimensional, i.e., one parameter, comparison of either pressure, flow, or volume to a trigger threshold is disadvantageous in that it is susceptible to random fluctuations in the monitored parameter, which may result in false triggers or cycles. In which case, an operator must intervene to reduce the trigger and/or cycle thresholds or ventilator sensitivity. However, reducing the ventilator's sensitivity can result in a greater amount of patient effort being needed before a spontaneous patient inspiration or expiration is detected, which is also disadvantageous, because a patient on a ventilator often has a weakened respiratory system to begin with.

SUMMARY OF THE INVENTION

Accordingly, it is an object of the present invention to provide a medical ventilator system that overcomes the shortcomings of conventional ventilators with improved triggering and/or cycling capability. This object is achieved according to one embodiment of the present invention by providing a ventilator system that includes a gas flow generator adapted to provide a flow of breathing gas, a gas flow controller that controls the flow of breathing gas delivered to the patient responsive to a control signal, a patient circuit adapted to communicate the flow of breathing with an airway of the patient, a flow sensor adapted to measure the flow of breathing gas in the patient circuit and to output a first flow signal indicative thereof, a pressure sensor adapted to measure a pressure of the flow of breathing gas in the patient circuit and to output a first pressure signal indicative thereof, and an exhaust assembly adapted to communicate gas from within the patient circuit to ambient atmosphere. The ventilator system also includes a controller that receives the first flow signal and the first pressure signal and outputs the control signal that controls the flow of breathing gas delivered to the patient circuit by the pressure generating system and, hence, the flow of breathing gas at a patient's airway. In one embodiment, the controller detects the onset of the inspiratory phase of a patient's breathing cycle for triggering the inspiratory flow of breathing gas based on such a patient's inspiratory effort, which is determined based on both the first flow signal and the first pressure signal.

According to a further embodiment of the present invention, the controller arms or makes available for activation a plurality of triggering mechanisms over an expiratory phase of a breathing cycle to increase the ventilator system sensitivity to a patient initiated trigger as the expiratory phase of the breathing cycle progresses.

In a still further embodiment, the controller detects the onset of the expiratory phase for cycling the ventilator based on such a patient's expiratory effort, which is determined based on both the first flow signal and the first pressure signal. This cycling feature of the present invention can be done alone or in combination with the triggering feature noted above.

In yet another embodiment of the present invention, the controller dynamically adjusts the cycling threshold criteria on a breath by breath basis so that the ventilator cycles more closely in synchronization with the patient's expiratory effort. In this embodiment, the ventilator system monitors the patient pressure $P_{patient}$ and, more particularly, its rate of change at the end of the inspiratory phase, as well as changes in the patient flow $Q_{patient}$ at the beginning portion of the expiratory phase to determine if the ventilator cycling for that breath occurred before or after the patient began exhalation, and dynamically adjusts the cycling threshold criteria in the next breath to account for the cycling synchronization error in the previous breath.

It is yet another object of the present invention to provide a method of triggering or cycling a medical ventilator that does not suffer from the disadvantages associated with conventional triggering and cycling techniques. This object is achieved by providing a method that includes: (1) generating a flow of breathing gas, (2) providing the flow of breathing gas to a patient via a patient circuit, (3) controlling the flow of breathing gas delivered to a patient responsive to a control signal, (4) measuring the flow of breathing in the patient circuit and outputting a first flow signal indicative thereof, (5) measuring a pressure of the flow of breathing gas in the patient circuit and outputting a first pressure signal indicative thereof, (6) communicating gas from within the patient circuit to ambient atmosphere, (7) detecting the onset of the inspiratory phase of a patient's breathing cycle for triggering an inspiratory flow of breathing gas based on the patient's inspiratory effort, which is determined based on both the first flow signal and the first pressure signal, and (8) detecting the onset of the expiratory phase of a patient's breathing cycle for cycling purpose based on the patient's expiratory effort, which is also determined based on both the first flow signal and the first pressure signal. It should be noted that triggering and cycling can be done independently or they can both be done during the appropriate stages of the breathing cycle.

According to a further embodiment of the present invention, a plurality of triggering mechanisms are made active during different stages of the expiratory phase of the pateint's breathing cycle to increase the ventilator system sensitivity to a patient initiated trigger as the expiratory phase of the breathing cycle progresses.

In yet another embodiment, the present invention provides a medical ventilator system that cycles from providing an inspiratory flow of breathing gas to allowing an expiratory flow by comparing the patient flow and a cycle threshold criteria. The system further dynamically adjusts the cycling threshold criteria on a breath by breath basis based on changes in patient pressure $P_{patient}$ at the end portion of the inspiratory phase and based on changes in the patient flow $Q_{patient}$ at the beginning portion of the expiratory phase, which are indicative of whether the ventilator cycling for that breath occurred before or after the patient began exhalation. In this embodiment, the cycling threshold criteria are dynamically adjusted in the next breath to account for the cycling synchronization error in the previous breath.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PRESENTLY PREFERRED EMBODIMENTS OF THE INVENTION

Figure 1:
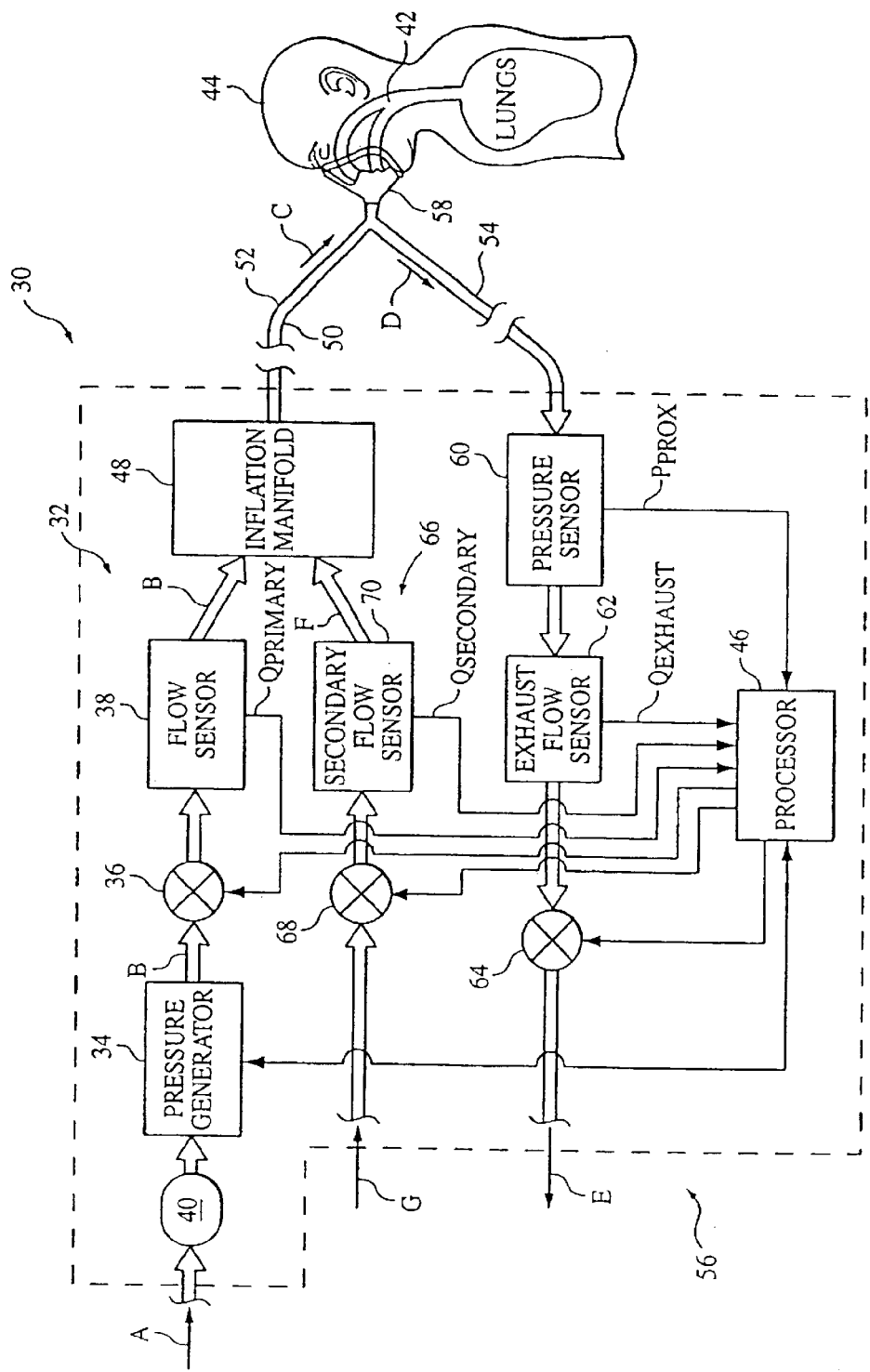
FIG. 1 is a schematic diagram of a ventilator system adapted to implement the triggering and cycling techniques of the present invention.

FIG. 1 schematically illustrates an exemplary embodiment of a ventilator system 30 according to the principles of the present invention. Ventilator system 30 is adapted to operate in an invasive mode, where the patient is typically intubated, or in a non-invasive mode, where the patient is not intubated. The basic components in ventilator 30 correspond to those found in a conventional ventilator, such as the Esprit® Ventilator manufactured by Respironics, Inc. of Pittsburgh, Pa., with the novel aspect of the present invention being the techniques used by the ventilator to trigger and/or cycle, such as utilizing recognition and quantification of physiologic-based concomitant multi-signal patterns, as opposed to a single signal pattern of conventional ventilators, for triggering purposes, cycling purposes, or both.

A. Ventilator System Hardware

Ventilator system 30 includes a primary gas flow delivery system, generally indicated at 32, which includes a pressure generator 34, a pressure/flow control element 36, and a flow sensor 38. Pressure generator 34 receives a flow of breathing gas, such as air, oxygen, or an oxygen mixture, as indicated by arrow A, through an optional muffler 40 or other noise suppression device from a supply of breathing gas (not shown). Pressure generator 34 elevates the pressure of the received breathing gas to generate a flow of breathing gas, as indicated by arrows B for delivery to an airway 42 of a patient 44.

In a preferred embodiment of the present invention, the pressure generator is a blower, which uses an impeller rotated by a motor to generate the flow of breathing gas at an elevated pressure relative to the ambient atmospheric pressure. It is to be understood, however, the present invention contemplates other devices and techniques for elevating or generating the flow of breathing gas, such as a piston, a bellows, and helical or drag compressor. The present invention further contemplates that the pressure generator can be a source of pressurized gas, such as air, oxygen or a gas mixture from a pressurized tank, a compressor, or from the wall outlet typically provided in a modern hospital. It can be appreciated that if the source of pressurized gas is from these latter sources, muffler 40 and pressure generator 34 can be eliminated and a pressure regulator may be required.

Pressure/flow control element 36, which is preferably downstream of pressure generator 34, controls the pressure or flow of breathing gas delivered to the patient. In a preferred embodiment of the present invention, pressure/flow control element 36 is a valve operating under the control of a processor 46. It is to be understood, however, that the present invention contemplates other techniques for controlling the flow of breathing gas delivered to an airway 42 of patient 44 by primary gas flow delivery system 32, such as modulating the flow of gas delivered to pressure generator, modulating the operating speed of pressure generator, or any combination of these techniques.

Flow sensor 38 is any suitable flow sensing device capable of quantitatively measuring the amount of fluid flowing therethrough and outputting a flow signal $Q_{primary}$ indicative thereof. In the illustrated exemplary embodiment, flow sensor 38 is downstream of pressure/flow controller 36. It is to be understood, however, that other locations and techniques for measuring the flow of breathing gas delivered to the patient by primary gas flow delivery system 32 are contemplated by the present invention, such as based on the operation of pressure/flow controller 36 or the energy provided to pressure generator 34.

In the illustrated exemplary embodiment, the flow of breathing gas, after being measured by flow sensor 38, is provided to an inhalation manifold 48 and delivered to patient 44 via a patient circuit 50. In a preferred embodiment of the present invention, patient circuit 50 is a two-limb circuit having an inspiratory limb 52 for carrying gas to the patient, as indicated by arrow C, and an expiratory limb 54 for carrying gas from the patient, as indicated by arrow D, to an exhaust assembly, generally indicated at 56. A patient interface device 58 communicates the patient circuit with the airway of the patient. The present invention contemplates that patient interface device 58 is any device, either invasive or non-invasive, suitable for communicating a flow of breathing gas from the patient circuit to an airway of the patient. Examples of suitable patient interface devices include a nasal mask, nasal/oral mask (which is shown in FIG. 1), full-face mask, tracheal tube, endotracheal tube, and nasal pillow.

Exhaust assembly 56 monitors and/or controls the venting of exhaust fluids to atmosphere, as indicated by arrow E, from expiratory limb 54 and includes a pressure sensor 60, an exhaust flow sensor 62 and an exhaust flow control element 64. Pressure sensor 60 measures the pressure $P_{prox}$ in expiratory limb 60 at a location proximal to the exhaust vent. For present purposes, pressure $P_{prox}$ is considered to correspond to the pressure at the patient $P_{patient}$. Pressure signal $P_{prox}$ is provided to processor 46. Of course, the pressure at the patient $P_{patient}$ can be measured directly via a pressure port in the patient interface device, for example.

Exhaust flow sensor 62, like flow sensor 38, is any suitable flow measuring device capable of quantitatively measuring the amount of fluid flowing therethrough and outputting a flow signal $Q_{exhaust}$ indicative thereof.

Exhaust flow control element 64 is preferably an active exhaust valve that can be selectively actuated to regulate the venting of exhaust gas to atmosphere under the control of processor 46. In particular, exhaust flow control element 64 preferably prevents fluid from exhausting to atmosphere when pressurized fluid is supplied to patient 44, i.e., during the inspiratory phase, and allows gas to escape to atmosphere at a controlled rate when the supply of pressurized fluid to patient 44 is terminated or reduced, i.e., during the expiratory phase. The active exhaust assembly preferably controls the flow of exhaust gas to atmosphere to control the positive end exhalation pressure ("PEEP") in the patient.

Ventilator system 30 in FIG. 1 includes an optional oxygen or secondary gas delivery system, generally indicated at 66, for delivering a supplemental or secondary gas flow, indicated by arrow F, concomitantly with the primary gas flow B. The oxygen or other secondary gas flow indicated by arrow G is delivered from a gas source (not shown), such as an oxygen tank or a wall outlet in a hospital, to a secondary gas flow control element 68, which is typically a valve. The pressure and/or flow of the secondary gas flow F is regulated by secondary gas flow control element 68 under the control of processor 46. The second gas flow is provided to inhalation manifold 48 where it is introduced or mixed with the primary gas flow, which together form the flow of breathing gas (arrow C) delivered to the patient. A secondary flow sensor 70 is provided for measuring the flow of secondary gas $Q_{secondary}$ provided to the inhalation manifold.

It should be noted that secondary gas delivery system 66 is optional and can be eliminated. However, in many practical ventilator implementations, it is desirable to deliver a flow of gas to a patient having a higher oxygen content than that available from the ambient atmosphere. In addition, medical gasses other than oxygen, can be delivered by secondary gas delivery system 66.

It is to be understood that the schematic diagram of a ventilator system shown in FIG. 1 is not intended to be a complete and exhaustive description of ventilator system, but is intended to describe the key components of the ventilator, especially those necessary to carry out the unique triggering and cycling techniques of the present invention. Those skilled in the art would understand, for example, that a medical ventilator system could also include features such as an input/output device for setting the operating parameters of the system, alarms (audible or visual) for signaling conditions of the patient or ventilator to an operator, as well as ancillary elements connected to the patient circuit, such as a humidifier, bacteria filter, an aspiration catheter, and a tracheal gas insufflation catheter, to name a few.

B. Ventilator System Operation

Figure 2:
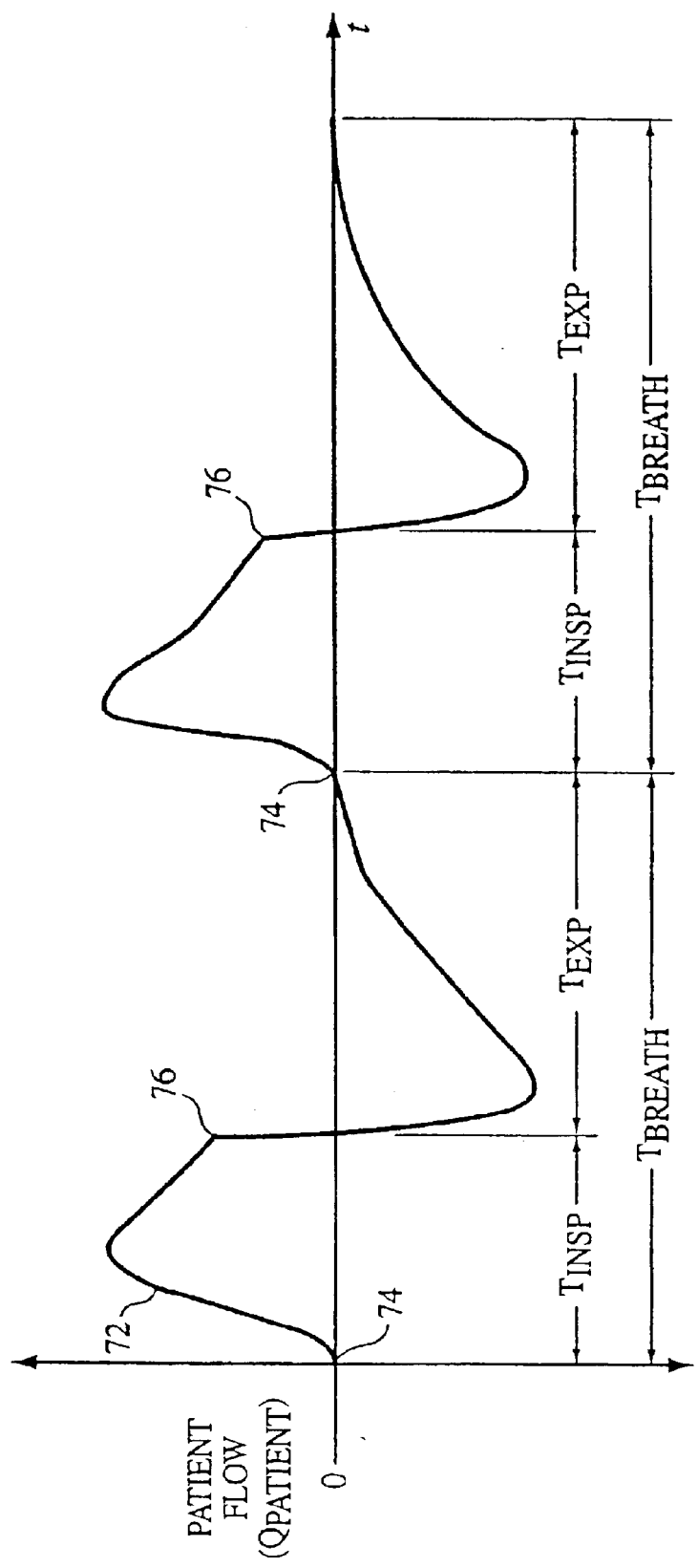
FIG. 2 is a waveform illustrating a typical patient flow of two normal, spontaneous respiratory cycles.

The operation of ventilator system 30 is discussed below with reference to FIGS. 3–4 and with continuing reference back to FIG. 1. However, before discussing the operation in detail, it is helpful to establish some basic terminology regarding a ventilated patient. To this end, FIG. 2 shows an exemplary waveform 72, illustrating the patient flow $Q_{patient}$ for two respiratory or breathing cycles in a normal, spontaneously breathing patient. Each breathing cycle $T_{breath}$ can be divided into four parts: (1) the transition from exhalation to inhalation, i.e., trigger point 74, (2) the inhalation or inspiratory phase, $T_{insp}$, (3) the transition from inhalation to exhalation, i.e., cycle point 76, and (4) the exhalation or expiratory phase $T_{exp}$.

The triggering and cycling techniques of the present invention control the process by which the ventilator system triggers from expiration to inspiration and cycles from inspiration to expiration, respectively, so that these events are synchronized with the breathing cycle of a spontaneously breathing patient. It is to be understood that the triggering and cycling techniques can be used independently of one another and can be used in conjunction with other functions present in a conventional ventilator, such as a timed backup breath should the patient fail to trigger the inspiratory flow after a set period of time, alarms, and other ventilation or pressure support modes. For example, in a pressure support or pressure assist mode of ventilation, one or both of the triggering and cycling techniques described herein are used. In a volume controlled mode of ventilation, only the triggering techniques of the present invention are utilized because cycling is timed, not spontaneous.

The triggering and cycling techniques of the present invention can also be used separately or concurrently in other modes of ventilation or pressure support such as: (1) proportional assist ventilation (PAV) mode, as taught, for example, in U.S. Pat. Nos. 5,044,362 and 5,107,830, both to Younes, the contents of each of which are incorporated herein by reference; (2) proportional positive airway pressure (PPAP) support as taught, for example, in U.S. Pat. Nos. 5,535,738; 5,794,615; and 6,105,575 to Estes et al., the contents of each of which are incorporated herein by reference; and (3) bi-level pressure support as taught, for example, by U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., the contents of each of which are incorporated by reference into the present invention.

As discussed in greater detail below, the ventilator triggering and cycling techniques of the present invention uses cross-correlatory patterns of patient flow $Q_{patient}$ and patient pressure $P_{patient}$ deviations from steady state as metrics for determining spontaneous, i.e., patient initiated, breath phase transitions. The use of both pressure and flow is believed to present a more accurate indication of the patient's respiratory effort as a trigger or cycle than is possible with conventional triggering or cycling techniques. In addition, the triggering and cycling techniques of the present invention efficiently detect patient initiated trigger and cycle events without erroneously interpreting noise or other system aberrations as such events.

Figure 3:
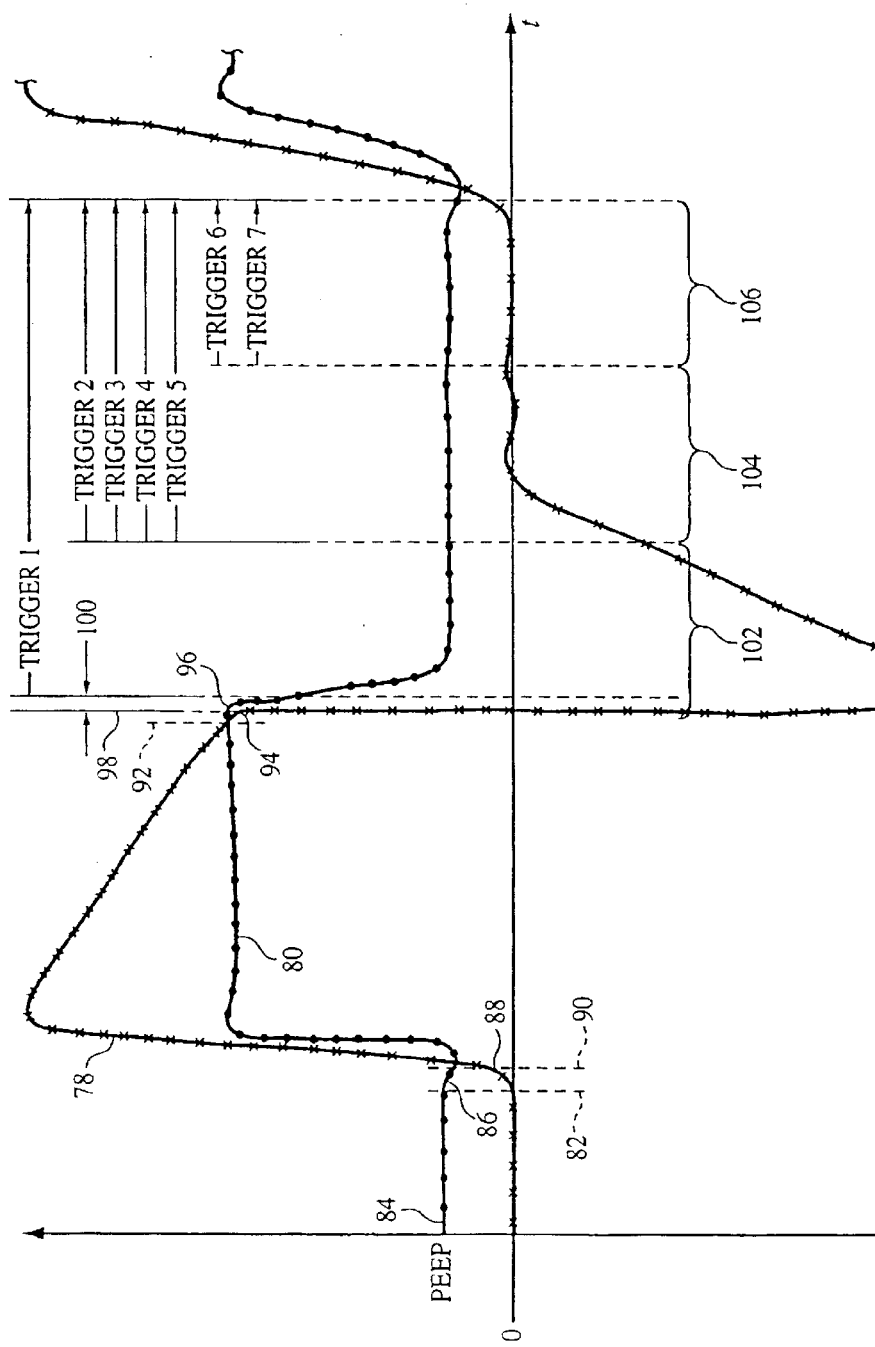
FIG. 3 is a waveform illustrating patient flow and patient pressure during a typical triggering process implemented by the ventilator system of FIG. 1 according to the principles of the present invention.

Referring now to FIG. 3, which shows patient flow $Q_{patient}$ 78 and patient pressure $P_{patient}$ 80, the present inventors noted that in the presence of a base flow, a patient's inspiratory effort, which begins at point 82, is indicated by a decrease in the patient pressure from the controlled pressure level 84, typically the PEEP level, followed by increasing flow into the lung. This decrease in pressure is indicated at 86 in FIG. 3 and the nearly concurrent increase in flow is indicated at 88. It should be noted that there is a small delay between the inception of the patient pressure drop and the rise in patient flow. The length of the delay can vary depending on the patient. For example, in patients suffering from COPD, the delay is longer than in other patients. Shortly, thereafter, at point 90, the ventilator triggers, and the patient flow and pressure increase. In one embodiment, the present invention uses this observable pressure drop and flow increase to trigger the ventilator, because this pressure-flow pattern indicates the patient has initiated an inspiratory effort.

The present invention contemplates using a similar, yet opposite, pattern that takes place at the end of the inspiratory phase of the breathing cycle to cycle the ventilator system from the inspiratory phase to the expiratory phase. More specifically, the present inventors noted that in a ventilated patient whose expiratory flow is controlled by an exhaust valve, the patient's expiratory effort, which begins at point 92, is indicated by a decrease in the patient flow, indicated at 94, followed by an increase in patient pressure, indicated at 96. This pressure-flow pattern indicative of a cycle event can be used to cycle the ventilator at point 98, causing the patient flow and pressure to decrease as expiration commences.

In another embodiment of the present invention, cycling the ventilator is accomplished based on patient flow and pressure changes at the end of inspiration. In this embodiment, discussed in detail below, the cycling threshold is dynamically altered on a breath by breath basis to maximize patient comfort as well as patient-machine synchrony.

The ventilator system of the present invention also provides other triggering mechanisms that are made active, i.e., begin searching for a triggering event, at different stages during the progression of the patient's expiratory cycle. These other triggering mechanisms preferably run concurrently with the pressure-flow triggering process of the present invention, so that a spontaneous trigger of the ventilator can take place whenever one of the trigger events occurs. This use of multiple triggering mechanisms becoming active due to the conditions that occur at various stages of the expiratory phase effectively causes the ventilator system's sensitivity to a patient initiated inspiratory effort for triggering purposes to be low at the start of the expiratory phase of the breathing cycle and increase as the patient progresses through the expiratory phase. As a result, false triggers are minimized while maximizing the system's responsiveness to the patient's inspiratory effort.

1. Patient Flow, Patient Pressure, and Leak

For purposes of the present invention, the patient pressure $P_{patient}$ is deemed to correspond to the proximal pressure $P_{prox}$ measured by pressure sensor 60. That is, $P_{patient}=P_{prox}$. Of course, $P_{patient}$ could be measured directly at the patient using any conventional technique. In ventilator system 30 shown in FIG. 1, patient flow $Q_{patient}$ is not measured directly in the same fashion as patient pressure, because it is not practical to place a flow meter at the patient's airway openings. Therefore, for this embodiment of the present invention, the actual patient flow $Q_{patient}$ is determined from the flows measured by flow sensors 38, 62, and 70. It is to be understood, however, that ventilator system 30 can be modified to provide a flow sensor near the patient. In which case, the patient flow $Q_{patient}$ is measured directly.

In a closed system, i.e., a system with substantially no or at least minimal, negligible leaks, such as ventilator system 30 of FIG. 1, the instantaneous patient flow $Q_{patient}$ is defined as:

$$Q_{patient}=Q_{primary}+Q_{secondary}-Q_{exhaust}. \qquad (1)$$

In this case, patient flow is directly determined without taking into consideration any systems leaks. This paradigm is generally applicable to a typical invasive ventilation system, because, in such a system, when set up properly, leaks are specifically intended to be minimized.

The present invention, however, contemplates including losses due to leaks into equation (1) so that the actual patient flow is determined more accurately by taking into consideration intentional and unintentional leaks. Intentional leaks, can include leaks through an exhaust port specifically provided in the patient circuit and/or patient interface to vent exhaust gas from the patient to atmosphere. A single-limb, non-invasive ventilator or pressure support device may include this type of exhaust port to allow the patient's expired gas to vent to atmosphere. Unintentional leaks can occur, for example, at the patient interface contact, such as between a mask seal and the patient's skin, and at couplings in the patient circuit. Taking into consideration leaks, equation (1) becomes:

$$Q_{patient}=Q_{primary}+Q_{secondary}-Q_{exhaust}-Q_{leak}, \quad (2)$$

where $Q_{leak}$ is the instantaneous leak flow, including intentional and unintentional leaks.

The present invention contemplates using any conventional technique for calculating leak flow $Q_{leak}$, such as those taught by U.S. Pat. No. 5,148,802 to Sanders et al., U.S. Pat. No. 5,313,937 to Zdrojkowski et al., U.S. Pat. No. 5,433,193 to Sanders et al., U.S. Pat. No. 5,632,269 to Zdrojkowski et al., U.S. Pat. No. 5,803,065 to Zdrojkowski et al., and U.S. Pat. No. 6,029,664 to Zdrojkowski et al., and pending U.S. patent application Ser. No. 09/586,054 to Frank et al., the contents of each of which are incorporated by reference into the present invention. Although one can refer to one or more of these references for a description of techniques for detecting and estimating leak and managing the delivery of breathing gas to the patient in the presence of leaks, a brief description of this process is provided below for the sake of completeness.

According to one leak estimation technique, $Q_{leak}$ in equation (2) at any given moments is determined as:

$$Q_{leak}=LF\sqrt{P_{patient}}, \quad (3)$$

where LF is a leak factor that is preferably calculated for each breath as:

$$LF = \frac{\int_0^{T_{breath}} (Q_{primary}+Q_{Secondary}-Q_{exhaust})\,dt}{\int_0^{T_{breath}} \left(\sqrt{P_{patient}}\right) dt}. \quad (4)$$

During a breathing cycle $T_{breath}$, processor 46 monitors the flow signals $Q_{primary}$, $Q_{secondary}$, and $Q_{exhaust}$ from flow sensors 38, 62, and 70 and the pressure signal $P_{prox}$ from pressure sensor 60. Using this information gathered over a complete breathing cycle, processor 46 determines the value for $$\int_0^{T_{breath}} (Q_{primary}+Q_{secondary}-Q_{exhaust})(t)\,dt$$

and $$\int_0^{T_{breath}} \sqrt{P_{patient}(t)}\,dt,$$

which are the terms in the numerator and denominator, respectively, for equation (4).

To determine a value for $Q_{leak}$ at any given instant in a breath cycle, processor 46 solves equation (3) utilizing the known value for LF from equation (4), which was calculated from the previous breathing cycle, and the measured flows and pressure at that instant. In an exemplary embodiment of the present invention, processor 46 samples the signals generated by flow sensors 38, 62 and 70 and pressure sensor 60 a plurality of times, for example, 100 samples per breath cycle or once every processing cycle, which takes place every 5 milliseconds (ms), to compute the patient flow from equation (2) essentially continuously.

It is to be understood that the present invention also contemplates using an average value of LF, rather than the leak factor determined in the immediately preceding breath cycle. For example, the leak factor for each of the last n breath(s) can be calculated and the average leak factor over the n breath(s) can be used in equation (3) to determine leak, where n is an integer. The present invention also contemplates that numerator, the denominator, or both in equation (4) can be determined from an average of these values determined during the last n breaths. In addition, the changes in leak factor can be made gradually, so that sudden changes in leak flow, do not result in abrupt changes in the leak factor or average leak rate used by the present invention While the technique described above for calculating the instantaneous patient flow $Q_{patient}$ is effective, it requires repeated recalculating of the leak factor LF, and determining the leak rate $Q_{leak}$ for each breathing cycle in order to determine the patient flow accurately. The present invention, however, contemplates another technique for calculating the patient flow $Q1_{pateint}$ under certain conditions that does not require a leak rate calculation. Namely, if ventilation system 30 is in a constant leak condition, which will occur where the patient pressure remains constant, the patient flow $Q1_{patient}$ is determined as follows. First, the net flow NetFlow(n) is determined as:

$$\text{NetFlow}(n)=Q_{total}-Q_{exhaust}, \quad (5)$$

where $Q_{total}=Q_{primary}+Q_{secondary}$, which is the total flow output under the control of the ventilator system.

Over a 100 ms moving window of time, a volume (Volume(n)) is calculated as follows:

$$\text{Volume}(n) = 0.005 * \sum_{n-19}^{n} \text{NetFlow}(k), \quad (6)$$

where n is processing cycle of 5 ms. Consecutive volume differentials (Volume Differentials(n)) are then calculated over a moving 50 ms window as:

$$\text{Volume Differential}(n)=\text{Volume}(n)-\text{Volume}(n-10). \quad (7)$$

According to this patient flow measurement technique, the net flow to the patient (equation (6)), which may or may not include a leak, from two different moving windows that are spaced closely together, are compared to one another (equation (7)). In doing this, the leak, which is constant and, thus, the same in each moving window, is cancelled out, so that the resulting difference, i.e., the Volume Differential represents the volume of fluid delivered to or received from the patient. The patient flow $Q1_{patient}$ is then determined on a continuous basis as:

$$Q1_{patient}=\text{Volume Differential}(n)/0.050+Q1_{patient(prior)}, \quad (8)$$

where $Q1_{patient(prior)}$ is the patient flow determined in the previous processing window.

The number, 0.050 in the denominator is selected because the window for the Volume calculation is a 50 ms window, with $Q1_{patient}$ being expressed in liters per second. As noted above, this technique for calculating patient flow is advantageous in that the patient flow can be calculated while effectively ignoring leak flow. However, the pressure must be stable in order to use this patient flow calculating technique.

Those skilled in the art can appreciate that either technique for determining patient flow, e.g., by determining patient flow $Q_{patient}$ including a leak or bias flow or by determining patient flow $Q1_{patient}$ that factors out leak or bias flow, can be used in the present invention. In general, patient flow $Q_{patient}$ or $Q1_{patient}$, both of which are also referred to as estimated patient flow, can be used interchangeably given stable leak conditions, except that patient flow $Q1_{patient}$ does not use any leak or bias flow estimation, while patient flow $Q_{patient}$ does. As will be noted below, there is at least one instance where this difference must be taken into account. See, e.g., Trigger #6 and the corresponding cycling technique.

Ventilator system 30 also uses the average leak rate $Q_{leak(average)}$ for various purposes discussed below, such as for providing a bias flow to the patient to compensate for leaks in the system. The average leak rate $Q_{leak(average)}$, which is the leak rate in liters per minute for a breathing cycle $T_{breath}$, is determined by first calculating the leak volume $V_{loss}$ during the breathing cycle. $V_{loss}$ is determined as:

$$V_{loss} = T_s \sum_{i=0}^{n} (Q_{primary} + Q_{secondary} - Q_{exhaust}), \quad (9)$$

where $T_s$ is the sampling period, i=0 is the first sample instance in the breathing cycle, and n is the last instance in the breathing cycle. The average leak rate $Q_{leak(average)}$ is then determined as $Q_{leak(average)} = (V_{loss}/T_{breath}) * 0.06$. The multiplier 0.06 is a conversion factor that is selected because $V_{loss}$ in the exemplary embodiment of the present invention is determined in milliliters and $T_{breath}$ is determined in second, while $Q_{leak(average)}$ is expressed in liters per minute. Those skilled in the art can appreciate that other conversion factors or no conversion factors may be used depending on the units being used. In the above example, the average leak rate is determined for each breath. It is to be understood, however, that an average leak rate can be calculated for more than one breathing cycle.

2. Bias Flow

In a preferred exemplary embodiment, the ventilator system of the present invention provides a bias flow to the patient so that a constant flow of gas is passing through the patient circuit. The magnitude of the bias flow is dependent upon the characteristics of the patient being ventilated, such as the patient's lung capacity, and the average leak rate $Q_{leak(average)}$. More specifically, for an adult patient, the bias flow is determined as the average leak flow in liters per minute plus a constant base rate, preferably 5 liters per minute. For a pediatric patient, the bias flow is determined as average leak flow plus a constant 3 liters per minute. In summary:

Adult: Bias Flow=$Q_{leak(average)}$+5 lpm

Pediatric: Bias Flow=$Q_{leak(average)}$+3 lpm.

In a preferred embodiment of the present invention, the value for the bias flow is recalculated for each breathing cycle and the new bias flow value is used to provide the bias flow in the next breathing cycle. In addition, for safety purposes, the average leak rate is bounded by a maximum value of 60 lpm, so that the maximum bias flow that can be provided to an adult, regardless of the actual average leak rate is 65 lpm and the maximum bias flow for a pediatric patient is 63 lpm.

Those skilled in the art can appreciate that the constant base rate added to the average leak rate need not be specifically limited to 5 and 3 for adult and pediatric patients, respectively. On the contrary, other values for the constant base rate can be selected depending on the size of the patient, for example, or other considerations, such as the condition of the patient. In addition, the constant leak rate can be eliminated or other selections, in addition to or in place of adult and pediatric, can be provided to the ventilator operator can more accurately match the requirements of the patient with the appropriate value for the constant base rate. In addition, the maximum average bias flow need not be specifically set to 60 lpm, rather other maximum values in this general range are contemplated by the present invention. Furthermore, the bias flow need not be recalculated every breathing cycle, but may be calculated more frequently or less frequently, so long as the effectiveness of the ventilator system is not compromised.

3. Triggering

The triggering process of the present invention is discussed below with reference to FIGS. 3–4. As shown in FIG. 3, the triggering process of the present invention effectively divides the exhalation phase $T_{exp}$ into the following four segments: 1) a restricted segment 100, 2) an active exhalation segment 102, 3) a non-active exhalation segment 104, and 4) a quiet exhalation segment 106. Establishing these segments in the expiratory cycle of the patient's breathing cycle is done to allow activation of one or more triggering mechanisms during each processing cycle based on the conditions that occur in each segment of the exhalation phase. FIG. 4 is a flowchart illustrating, in general, an exemplary triggering process implemented by the ventilator system. In a preferred embodiment of the present invention, all allowable trigger mechanisms, i.e., Triggers #1–#7, are armed so that they can be tested for activation during each processing cycle, and once a trigger is armed or enabled, it remains armed and awaiting activation for that processing cycle, and for the rest of the exhalation phase so long as the conditions needed to enable or arm the triggering mechanism remain satisfied.

Arming different triggering mechanisms during different phases of the expiratory phase causes the effective sensitivity of the ventilator system triggering mechanism to increase the further the patient goes into the expiratory phase of the breathing cycle. For example, it is unlikely that immediately after transitioning into the expiratory phase, the patient will attempt an inspiration. Therefore, the ventilator system's sensitivity to a spontaneous inspiration at that time need not be very high. On the other hand, when the patient nears the end of the expiratory phase, it is very likely that that patient will soon be attempting to make a spontaneous inspiratory effort. Therefore, the ventilator system's sensitivity to detecting an inspiratory effort should be maximized at the end of the expiratory phase to detect the inspiratory effort reliably while minimizing the effort required by the patient to trigger the ventilator. FIG. 3 illustrates when the various triggers effectively become active during the various stages of the expiratory cycle. The operational definition of each segment of the exhalation phase $T_{exp}$ is discussed in turn below.

In the present invention, there are four basic types of trigger mechanisms: a pressure trigger, a flow trigger, a volume trigger, and an effort trigger. Trigger #1 is a pressure trigger that tests the patient pressure against a threshold pressure with a relatively high sensitivity level. Trigger #2 is a flow trigger that tests the patient flow against a threshold flow. Triggers #3 and #4 are volume triggers that test a volume against a threshold volume. More specifically, Trigger #3 tests the estimated patient inhaled volume over the course of an increasing patient flow pattern against a threshold volume, and Trigger #4 tests the inhaled patient volume over 50 ms against a threshold volume. As such Trigger #3 is more of a long term trigger, looking as longer term trends in the patient, and Trigger #4 is more of short term trigger, looking at the patient's more immediate volume. The effort trigger refers to a determination of the patient's inspiratory effort based on a cross correlation of patient pressure and patient flow, which is compared to a threshold effort level to determine whether to trigger the ventilator. Triggers #5, #6 and #7 are effort based triggers, with Triggers #5 and #7 being longer term triggers, looking at patient effort over longer period of time, than Trigger #6, which is a short term effort trigger that looks at the amount of inspiratory effort the patient is exerting over a short period of time.

The following parameters are used in implementing the triggering algorithm of the present invention, and are constrained as defined below.

CompFlow: −1 lpm or −5% of the average leak $Q_{leak\ (average)}$, whichever is algebraically smaller.

MinFloT2: −4 lpm if $Q_{leak(average)}$ is less than 30 lpm, 0 lpm otherwise.

Beta: 0.1 ml if expiration time≦inspiration time, otherwise: Beta=0.2 ml if Bias Flow <15 lpm; or Beta=0.5 ml if Bias Flow ≧15 lpm and <30 lpm; or Beta=1 ml if Bias Flow ≧30 lpm.

MinStTime: 100 ms if $Q_{leak}$<30 lpm or 200 ms if $Q_{leak}$≧30 lpm.

MinTimeT3: 150 ms if $Q_{leak}$<30 lpm or 250 ms if $Q_{leak}$≧30 lpm.

MinVolT3: 3 ml if $Q_{leak}$<60 lpm or 4 ml if $Q_{leak}$>60 lpm.

Sigma: Pediatrics: Sigma=1 $cmH_2O*lpm$. Adult: Sigma=1 $cmH_2O*lpm$ if $Q_{leak}$<30 lpm, and Sigma=3 $cmH_2O*lpm$ if $Q_{leak}$≧20 lpm.

It should be understood that the values for the above parameters are dependent on the physical characteristics of the components used in ventilator system 30. For example, the configuration of the exhaust flow control element, i.e., the exhaust valve, and/or the tubing used in the patient circuit can affect the specific values of these parameters. Thus, the present invention is not intended to be limited to the specific values of the parameters set forth above, but can encompass a range of values so long as the ventilator system functions in accordance with the principles of the present invention. In addition, the present invention contemplates that the values for these parameters can be adaptive, to maximize the operation of the ventilator, or they can be manually controllable to allow the ventilator operator a great degree of flexibility in setting up the ventilator to suit the needs of any given patient.

Figure 4:
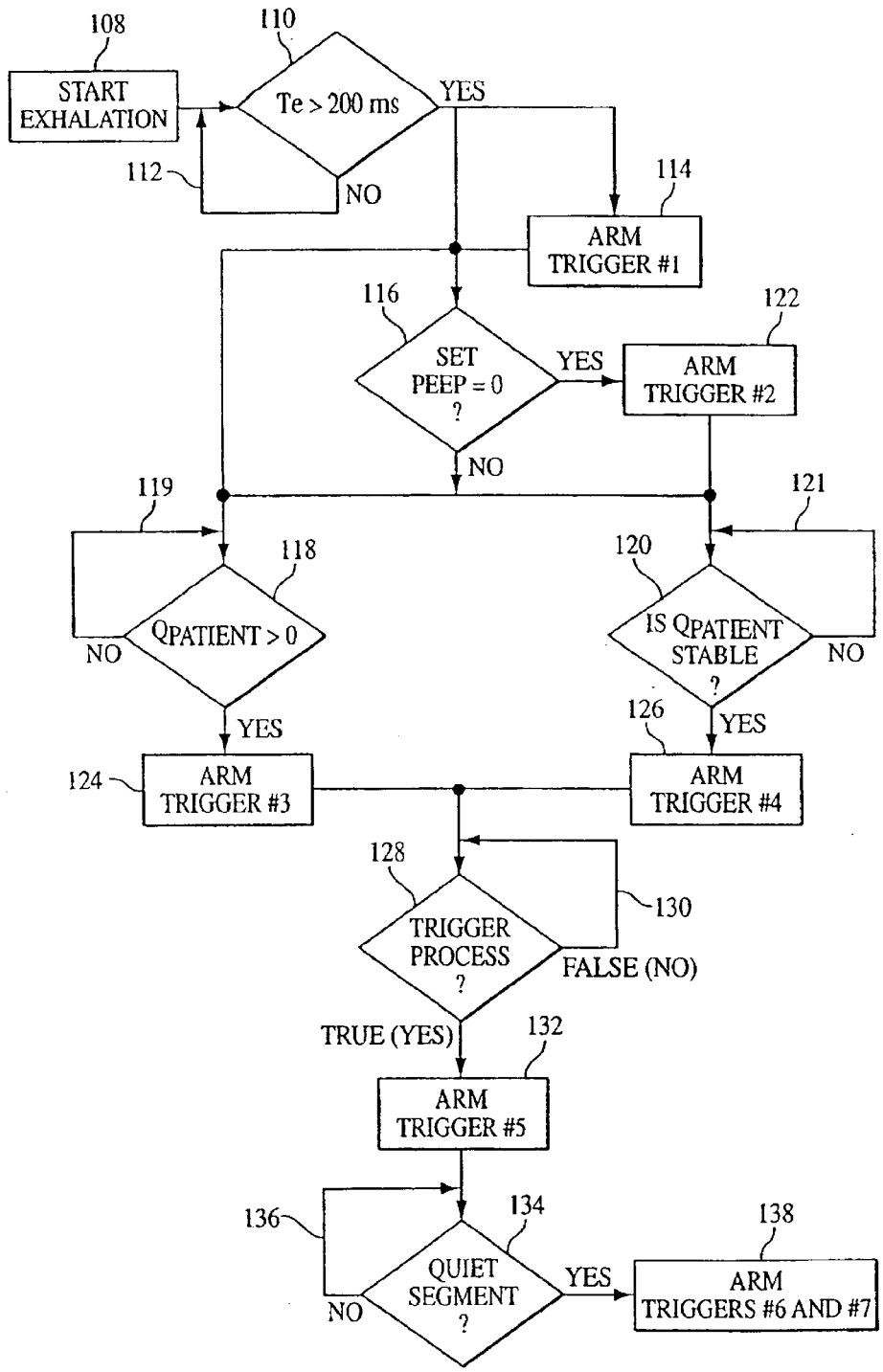
FIG. 4 is a flowchart of a triggering process implemented by the ventilator system of FIG. 1.

Referring now to FIGS. 3 and 4, restricted segment 100 is a short duration at the outset of the exhalation phase, which begins at a cycle point 98, during active exhalation segment 102. In restricted segment 100, no triggers from expiation to inspiration are permitted. In a preferred embodiment of the present invention, the restricted segment is set to 200 ms. It is to be understood, however, that the duration of the restricted segment can vary over a range of values around this general time frame. The 200 ms time frame is selected in the present invention because for the most part, a human being is physically unable to return to the inspiratory cycle within this short of a time frame after commencing the expiratory cycle.

In step 108, exhalation begins, and in step 110, processor 46 determines whether 200 ms have elapsed since the start of exhalation. If not, the expiratory flow is still within the restricted segment, and step 10 is repeated until the duration of the restricted segment has elapsed, as indicated by feedback loop 112. If 200 ms have elapsed since the start of exhalation, the processor continues to steps 114, 116, 118, and 120.

After the 200 ms delay, i.e., restricted segment 100, the patient enters the unrestricted portion of active exhalation segment 102. Active exhalation segment 102 is defined as the interval, following the end of the restricted segment, during which the flow through exhaust flow control element 64 $Q_{exhaust}$ exceeds the total delivered flow $Q_{total}$ by more than 5 liters per minute (lpm). This is the interval of the expiratory phase that the patient is actively expelling gas from the lungs. To be conservative, leak $Q_{leak}$ is not considered in determining if the patient is in the active exhalation segment.

In active exhalation segment 102, Trigger #1, which is a backup pressure trigger is armed, i.e., made ready for activation should the proper conditions occur, as indicated in step 114. Trigger #1 is a conventional pressure trigger with a sensitivity of 3 $cmH_2O$, so that if the patient pressure $P_{patient}$ is less than the set PEEP level by 3 $cmH_2O$ or more, the ventilator triggers. It can be appreciated that Trigger #1 requires a relatively large amount of patient effort in order to decrease the patient pressure 3 $cmH_2O$ to prevent false triggers. Such false triggers are likely to occur if the ventilator's trigger sensitively is too high, because the active exhalation segment represents a portion of the expiratory phase where patient flow is relatively unstable, i.e., flow rates can differ greatly over relatively short periods of time.

In step 116, processor 46 determines if the PEEP is to set to zero. If so, Trigger #2, which is a conventional flow backup trigger of 2 lpm is armed in step 122. According to Trigger #2, if the patient flow $Q_{patient}$ is positive and, if the patient flow is more than 2 lpm, the ventilator will trigger. It can be appreciated that even though Trigger #2 is first checked during active exhalation segment 102, Trigger #2 cannot be used to trigger the ventilator until the patient is in non-active exhalation segment 104, because the patient flow will not be positive during the active exhalation segment. Those skilled in the art can further appreciate that this trigger is optional depending on the operating characteristics of the ventilator being used to implement the teachings of the present invention.

According to the present invention, a patient is in non-active exhalation segment 104 when the patient flow $Q_{patient}$ exceeds a certain minimum threshold CompFlow, which, as noted above, is −1 lpm or −5% of the average leak $Q_{leak\ (average)}$, whichever is algebraically smaller. The patient is also considered to be in non-active exhalation segment 104 when (1) the exhaust flow $Q_{exhaust}$ is less than the delivered flow $Q_{total}$+5 lpm and (2) the volume differential, a 100 ms Volume Differential(n), (see equation (7)) has stabilized for at least a certain amount of time. The Volume Differential(n) is considered to be stable if, for example, consecutive absolute values of Volume Differential(n) are less than 0.1 ml for an amount of time MinStTime, which as noted above, is 100 ms if $Q_{leak}$ is less than 30 lpm, or 200 ms if $Q_{leak}$ is greater than or equal to 30 lpm.

In step 118, the ventilator system determines if the patient flow $Q_{patient}$ is positive. If so, Trigger #3 is armed in step 124. If not, the system re-checks every processing cycle, as indicated by feedback loop 119. According to Trigger #3, if the patient flow starts to rise, its initial value is saved as a reference flow $Q_{ref}$. Then, the difference between the current flow $Q_{patient(current)}$ and the reference flow $Q_{ref}$ is accumulated during each processing cycle n, which in an exemplary embodiment is 5 ms.

Accumulating this difference ($Q_{patient(current)}$−$Q_{ref}$) continues in subsequent processing cycles, so long as all three of the following conditions are met: 1) the patient flow $Q_{patient}$ is greater than the reference flow $Q_{ref}$, 2) the Volume Differential(n) is greater than 0, and 3) the amount by which the current patient flow exceeds a prior patient flow is greater than a certain amount, i.e., the slope of the flow increase is at least a certain value. In a preferred embodiment of the present invention, this third condition is determined by comparing the current patient flow $Q_{patient}(n)$ to the sum of a (1) time-delayed patient flow $Q_{patient(delayed)}(n)$ and a (2) constant flow rate, such as 0.5 lpm, i.e., $Q_{patient}(n) > Q_{patient(delayed)}(n) + 5$ lpm, where n is one processing cycle of 5 ms. In this embodiment, $Q_{patient(delayed)}(n) = 0.2 Q_{patient}(n) + 0.8 Q_{patient(delayed)}(n-1)$. If any one of these conditions is not met, Trigger 3# is reset, which causes $Q_{ref}$ to reset and the accumulated values to be reset to zero.

The accumulated values of the difference ($Q_{patient(current)} - Q_{ref}$) correspond to the patient volume because a difference ($Q_{patient(current)} - Q_{ref}$) is determined every 5 ms, i.e., each processing cycle. To obtain the volume, the difference is multiplied by time, such as 5 ms for one processing cycle. If the running sum of patient volume exceeds a threshold volume, such as 7 ml in a preferred embodiment of the present invention, over any length of time, a trigger is declared. As noted above, the patient running volume sum is reset if any of the above three conditions is breached.

In step 120, the Volume Differential(n) is monitored to determine if it has remained stable for a period of time MinTimeT3, which, as noted above, is 150 ms if the leak $Q_{leak}$ is less than 30 lpm or 250 ms if $Q_{leak}$ is greater than or equal to 30 lpm. The Volume Differential(n) is considered to be stable if, for example, consecutive absolute values of Volume Differential(n) are less than 0.1 ml for an amount of time MinTimeT3. If so, Trigger #4 is armed in step 126. If not, the system re-checks every processing cycle, as indicated by feedback loop 121. According to Trigger #4, if the 50 ms Volume Differential(n) exceeds MinVolT3, which, as noted above, is 3 ml if $Q_{leak}$ is less than 60 lpm or 4 ml if $Q_{leak}$ is greater than or equal to 60 lpm, then a trigger is declared.

If the patient is still in non-active exhalation segment 104 as determined according to the criteria set forth above, i.e., if the patient flow is level or the stability conditions are satisfied, a search to determine whether a "trigger process" is conducted in step 128. This is only done if a valid trigger process is not indicated as having been detected, i.e., a trigger process flag is false. A trigger process corresponds to a situation where the patient flow is increasing and the proximal pressure is decreasing.

According to an exemplary embodiment of the present invention, detecting a valid trigger process requires that all three of the following conditions during a current processing cycle n be satisfied:
1) $Q_{patient}(n-10) > $ CompFlow;
2) $P_{patient}(n-10) \leq 1.2*$set PEEP or $0.5 H_2O$ (whichever is bigger); and
3) $Q_{patient}(n) > Q_{patient}(n-10)$, and $[P_{patient}(n-10) - P_{patient}(n)] > 0.3$ or $P_{patient}(n) < 0.8$ set PEEP.

The first condition requires that the patient flow 50 ms prior to the current patient flow is greater than CompFlow. The second condition requires that the patient pressure 50 ms prior to the current patient pressure is less than or equal to 120% of the set PEEP level or $0.5 H_2O$, whichever is bigger. The third condition requires that the patient flow be increasing, i.e., $Q_{patient}(n) > Q_{patient}(n-10)$, and that the patient pressure be decreasing, i.e., $P_{patient}(n-10) - P_{patient}(n)$ or less than 80% of the set PEEP. If the three conditions set forth above are satisfied, a trigger process is declared, i.e., the trigger process flag is set to true. In which case, the patient flow at the start of the trigger process $Q_{patient}(n-10)$ is set as a reference flow $Q_{ref}$ and the patient pressure at the start of the trigger process $P_{patient}(n-10)$ is set as a reference pressure $P_{ref}$. If the three conditions set forth above are not satisfied, a trigger process is not declared, i.e., the trigger process flag is set to false, and the system re-checks for a trigger process every processing cycle, as indicated by feedback loop 130.

If a valid trigger process is indicated as having already been detected, i.e., a trigger process flag is true when step 128 in the current processing cycle is reached, then in the current processing cycle, the current patient flow $Q_{patient}(n)$ is compared to the reference flow $Q_{ref}$ and the current patient pressure $P_{patient}(n)$ is compared to the reference pressure $P_{ref}$. If $Q_{patient}(n) \geq Q_{ref}$ and $P_{patient}(n) \leq P_{ref}$, then a test for a trigger, such as Triggers #5, #6 and #7, can be made.

In step 132, which is reached as long as the trigger process remains true, an effort based Trigger #5 is armed. According to Trigger #5, the product of a patient flow difference ($Q_{patient} - Q_{ref}$) and a pressure difference ($P_{ref} - P_{patient}$) is calculated and compared against a leak-based threshold to determine a valid trigger. In a preferred embodiment, this threshold is $1.0 \text{ cmH}_2\text{O*ml/s}$. So that if $(Q_{patient} - Q_{ref})*(P_{ref} - P_{patient})$ is greater than $1.0 \text{ cmH}_2\text{O*ml/s}$, a trigger is declared.

The following conditions must be met in order for checking this trigger:
1) $Q_{patient} \geq $ CompFlow;
2) $P_{patient} < 0.3 \text{ cmH}_2\text{O}$ or $1.2*$set PEEP (120% of set PEEP) whichever is bigger; and
3a) $Q_{patient} > $ MinFloT2, or
3b) the volume based stability condition for establishing that the patient is in the non-active exhalation segment has been met.

In step 134, the ventilation system checks to determine whether the patient is in quiet exhalation segment 106 by checking the following conditions:
1) $Q_{exhaust} < Q_{total} + 5$ lpm;
2) $Q_{patient} > $ CompFlow;
3) Volume Differential has remained stable for at least MinStTime; and
4) The sum of the absolute values of Volume Differentials over 50 ms is less than Beta.

If these conditions are not met, the system re-checks for a quiet segment every processing cycle, as indicated by feedback loop 136. If, however, all of these conditions are met, then the patient is deemed to be in quiet exhalation segment 106 and the system proceeds to step 138.

In addition to the triggering options already armed as discussed above, two other effort based triggering options Triggers #6 and #7 are armed in step 138. These two effort based triggering algorithms are based on the comparison of a measure of the estimated patient effort using two different patient flow estimation methods and time scales so that a short term effort trigger (Trigger #6) and a longer term trend based effort trigger (Trigger #7) are provided in step 138. More specifically, in step 138, if the differential patient effort over 100 ms exceeds a leak based threshold (short term effort Trigger #6), then a trigger is declared. Also in step 138, if the accumulated patient effort, which is the time integral of the product of patient flow deviation from a reference and patient pressure deviation from a reference (longer term effort Trigger #7) exceed a leak based effort threshold, then a trigger is declared.

According to Trigger #6, when the quiet exhalation has been established (step 134) and the trigger process is holding true, the Estimated Patient Effort (EPE) over a 100 ms window is compared against a constant threshold (sigma). If EPE equals or exceeds sigma, a trigger is declared. In one embodiment of the present invention, the EPE is determined as the sum of the products of a patient flow difference $\Delta Q_{patient}$ and a filtered, i.e., delayed, pressure difference ($F\Delta P_{patient}$) over a 100 ms interval.

The purpose of the filtering is to delay the patient pressure used in the pressure difference function, because, as noted above, at the onset of inspiration there is a small delay between the onset of the pressure drop and the rise in patient flow. This delay allows the current patient flow to be multiplied by a patient pressure difference that is determined using a patient pressure that corresponds to the current patient flow. The pressure difference is measured between the pressure reference $P_{ref}$ at the start of the trigger window (see step 128) and the current patient pressure $P_{patient}$.

EPE is determined every processing cycle, e.g., every 5 ms. At control cycle n:

$$EPE(n) = \sum_{n-19}^{n} F\Delta P_{patient}(n) * \Delta Q_{patient}(n), \qquad (10)$$

where, $$\Delta P_{patient}(n) = P_{ref} - P_{patient}(n), \qquad (11)$$

$$F\Delta P_{patient}(n) = 0.33\ \Delta P_{patient}(n) + 0.67\ F\Delta P_{patient}(n-1), \text{ and} \qquad (12)$$

$$\Delta Q_{patient}(n) = Q_{patient}(n) - Q_{ref} \qquad (13)$$

$Q_{patient}(n)$ is the current patient flow and $Q_{ref}$ is the patient flow at the start of the triggering window, see step 128. Equation (12) represents a digital filter of pressure differential $\Delta P(n)$, which as noted above, is provided to introduce a delay in patient pressure components of the estimated patient effort calculation. For purposes of Trigger #6, $Q_{patient}$ is set to zero ($Q_{patient}$=0) if either (a) $Q_{patient}$<0 or (b) $Q_{patient}$<3 ml/s and $F\Delta P_{patient}$<0.2 cmH$_2$O.

If patient flow is determined as discussed above with respect to equation (8), i.e., the estimated patient flow $Q1_{patient}$ factors out any stable bias or leak flow, or if there is no leak or bias flow, e.g., the patient flow is measured directly at the patient, then $Q_{ref}$ in equation (12) is effectively zero. That is, it is assumed that the reference flow at the start of the trigger window is zero, and the system need only look for an increase from this baseline or zero value. In which case, EPE is determined as:

$$EPE(n) = \sum_{n-19}^{n} F\Delta P_{patient}(n) * Q1_{patient}(n), \qquad (14)$$

where $Q1_{patient(prior)}$ from equation (8) is set equal to zero at the start of the trigger window. As noted above, if EPE(n) determined using either equation (10) or (14) is greater than sigma, a trigger is declared.

According to Trigger #7, under the quiet exhalation condition, when a trigger process is established as true, as long as the trigger process stays true, the product of ($Q_{patient}$-$Q_{ref}$)*($P_{ref}$-$P_{patient}$) is accumulated from each processing cycle. If this running sum equals or exceeds 1.5 cmH$_2$O*ml/s a trigger is declared. In this way, a relatively long term patient effort trend is monitored for a triggering event.

4. Cycling

The present invention contemplates using one of following two cycling techniques to transition from the inspiratory phase to the expiratory phase of the breathing cycle: 1) an effort based technique that is based on the combination of patient flow and patient pressure, and 2) an adaptive, flow based technique where cycling is determined by comparing the current patient flow to a threshold flow. Essentially, the function of the cycling event is to cause the ventilator to allow patient flow to be expelled from the lungs. This is accomplished in ventilator system 30, for example, by opening or increasing the degree of opening of exhaust flow control element 64 at the time the patient begins the expiratory effort.

The effort based cycling technique was discussed briefly above and is essentially the same as Triggers #5, #6, and #7, except that a cycle event is indicated by an algebraic decrease in flow followed by an increase in pressure. Thus, the patient flow is delayed by a small time factor before the product of the patient flow and patient pressure difference over a certain time frame is determined and compared to a threshold expiratory effort level.

More specifically, cycling in a manner similar to Trigger #5 discussed above involves determining a patient flow difference ($Q_{ref}$-$Q_{patient}$) and patient pressure difference ($P_{patient}$-$P_{ref}$). The product of these differences ($Q_{ref}$-$Q_{patient}$)*($P_{patient}$-$P_{ref}$) is determined and compared to a threshold to determine a valid cycle. The threshold value is preferably determined empirically based on clinical trials and can be made adaptive to match the changing conditions of the patient.

Cycling in a manner similar to Trigger #6 discussed above involves determining a patient pressure difference ($P_{patient}$-$P_{ref}$) similar to that done in equation (11), where $P_{patient}$ is the current patient pressure and $P_{ref}$ is a reference patient pressure determined at a start of a cycling window. In addition, a patient flow difference ($Q_{ref}$-$Q_{patient}$) similar to that done in equation (13) is determined, wherein $Q_{patient}$ is the current patient flow, and $Q_{ref}$ is a reference patient flow determined at the start of the cycling window. Of course, $Q_{ref}$ is only used if the determination of patient flow does not already automatically eliminate any bias flow or there is a leak or bias flow that should be compensated for.

It should be noted that for cycling purposes, the system looks for a pressure increase from the reference pressure set at the start of the cycling window. Therefore, $P_{ref}$ is subtracted from $P_{patient}$, rather than subtracting $P_{patient}$ from $P_{ref}$ as done in Equation (11), to ensure that this patient pressure difference is indicative of a pressure increase. The system also looks for a flow decrease from the reference flow set at the start of the cycling window, i.e., an increase in expiratory flow from the patient. Therefore, $Q_{patient}$ is subtracted from $Q_{ref}$, rather than subtracting $Q_{ref}$ from $Q_{patient}$, as done in equation (13).

As noted above, for cycling/expiratory effort determination purposes, the present invention delays the patient flow and determines a product of the current patient pressure difference and the delayed patient flow as the patient's expiratory effort. This expiratory effort, which is preferably determined every processing cycle (i.e., every 5 ms), is summed over a very short time interval, such as 100 ms. Cycling from providing the inspiratory flow to allowing an expiratory flow of breathing gas from the exhaust assembly is initiated if the sum of the patient's expiratory efforts over this short time interval exceed a threshold. The value of this threshold can be determined empirically and can be made adaptive to match the changing conditions of the patient.

Cycling in a manner similar to Trigger #7 discussed above, which looks at a longer term expiratory effort trend, involves determining a patient flow difference ($Q_{ref}$-$Q_{patient}$), where $Q_{patient}$ is the current patient flow and $Q_{ref}$ is a reference patient flow determined at the start of the cycling window. It should be again noted that for cycling purposes, the system looks for a flow decrease, i.e., increasing expiratory flow from the patient, from the reference flow set at the start of the cycling window. Therefore, $Q_{patient}$ is subtracted from $Q_{ref}$, rather than subtracting $Q_{ref}$ from $Q_{patient}$, to ensure that this patient flow difference is indicative of increasing expiratory flow.

The system further determines a patient pressure difference ($P_{patient}-P_{ref}$), where $P_{patient}$ is the current patient pressure from the first pressure signal and $P_{ref}$ is a reference patient pressure determined at the start of the cycling window, again looking for an increase in patient pressure above the reference value determined as the start of the cycling window. The patient's expiratory effort is determined as a product of the patient flow difference and the patient pressure difference. As done with Trigger #7, the system continues to sum these patient expiratory efforts over at time interval and initiates a cycle if the sum of the patient's expiratory efforts over the time interval exceed a threshold. This threshold is also determined empirically, and can be made adaptive.

Under the adaptive, flow based technique, the cycle threshold flow (CTF) is set as a percentage of the peak flow for that breath. In a preferred embodiment of the present invention, the CTF is initially set at 35% of the peak inspiratory flow. The patient flow during the inspiratory phase is monitored, and once this flow falls below the cycle threshold flow, the ventilator cycles. The present inventors recognized that the CTF level cannot be fixed at this level, because the patient is unlikely to always begin exhaling when their flow falls to 35% of their peak flow for that breath. Accordingly, the present inventors developed a process to dynamically adjust the CTF.

To allow the CTF to adapt so that the ventilator cycles more closely in synchronization with the patient's expiratory effort, the present invention monitors the patient pressure $P_{patient}$ at the end portion of the inspiratory phase and the patient flow $Q_{patient}$ at the beginning portion of the expiratory phase. If the patient pressure begins to increase before the patient flow reaches the CTF, this indicates that the patient has begun exhalation and the exhaust flow control element has not yet been opened to permit the patient to exhale freely. In other words, the ventilator cycled too late, i.e., after the patient began exhaling. On the other hand, if the ventilator has cycled and there is substantially no patient flow from the patient, this indicates that the patient has not yet begun to exhale even though the exhaust flow control element has been opened. In other words, the ventilator cycled too early, i.e., before the patient began exhaling. The present invention monitors the patient pressure and flow to determine if either of these errors in synchronization have occurred, and adjusts the CTF in the next breath to account for the cycling synchronization error in the previous breath.

To determine whether the ventilator cycled too late, the patient pressure at the end of the inspiratory phase $P_{patient\ (insp\ end)}(k)$ and the patient pressure at a time, such as 100 ms, before the end of the inspiratory phase $P_{patient(insp\ end)}(k-100)$ are obtained. If $P_{patient(insp\ end)}(k) > P_{patient(insp\ end)}(k-100)+0.5$ cmH$_2$O, the ventilator cycled too late. In a preferred embodiment of the present invention, when this occurs, the CTF is increased a predetermined amount, for example 20% so that the ventilator cycles sooner in the next breathing cycle.

To determine whether the ventilator cycled too early, the volume of fluid from the patient during the initial portion of the expiratory phase $V_{exp}(k)$ is compared to a percentage, such as 25%, of a volume of fluid inspired by the patient during a similar time period in the preceding inspiratory phase $V_{insp}$th. If the ventilator cycled too early, the volume of fluid from the patient during the initial portion of the expiratory phase will be less than the volume of fluid inspired by the patient during a similar time period in the preceding inspiratory phase.

In a preferred embodiment of the present invention, the volume of fluid from the patient during the first 300 ms of the expiratory phase $V_{exp}(k)$ is determined as:

$$V_{exp}(k) = \int_0^{300\ ms} Q_{patient}(t)\,dt. \quad (13)$$

Twenty-five percent of prorated inhaled patient volume estimate for 300 ms of the inhalation period $V_{insp}$th is determined as:

$$V_{insp}th = \left(\frac{75}{T_{insp}}\right)\left\{\int_0^{T_{insp}}(Q_{primary}+Q_{secondary}-Q_{exhaust})\,dt - T_{insp}*LF*\sqrt{P_{patient(insp\ end)}}\right\}, \quad (14)$$

where $P_{patient(insp\ end)}$ is the end inspiratory pressure, which is assumed to correspond to the average patient pressure over the length of the inspiratory phase. It is to be understood, however, that the average patient pressure over the length of the inspiratory phase can be determined directly so that an approximation need not be used. In a preferred embodiment of the present invention the value for $V_{insp}$th is bounded as follows.

adult: 40 ml $\leq V_{insp}$th $\leq$ 200 ml, and
pediatric: 10 ml $\leq V_{insp}$th $\leq$ 40 ml.

If the ventilator did not cycle too late, $V_{exp}(k)$ is compared to $V_{insp}$th. It should be noted that $V_{exp}(k)$ and $V_{insp}$th will have opposite signs, because $V_{exp}(k)$ represents a volume exhaled and $V_{insp}$th represents a volume inhaled. If the absolute value of $V_{exp}(k)$ is less than the absolute value of $V_{insp}$th, then the patient is not trying to exhale, i.e., the ventilator cycled too soon. In which case, the CTF is decreased a predetermined amount, for example 10%, so that the ventilator cycles later in the next breathing cycle. If the ventilator did not cycle too late, and if the absolute value of $V_{exp}(k)$ is not less than the absolute value of $V_{insp}$th, then the CTF remains unchanged.

It is to be understood that the amount and rates at which the CTF is increased and decreased can be varied depending on how aggressively the ventilator should attempt to correct for cycling synchronization errors. It is preferable, however, that the CTF be bounded, for example, between 3% and 60% of the peak flow for that breath. 300 ms is used for the time period of the window at the beginning of the exhalation phase during which the patient's flow/volume is monitored is selected because it is likely that a patient who is attempting to exhale will produce measurable results within 300 ms of beginning to exhale.

It is to be understood, that cycling can also be accomplished using conventional cycling techniques. However, under the cycling option of the present invention, the cycling criteria are adaptively altered based on conditions obtained from the previous breath for maximum patient comfort.

The triggering and cycling parameters discussed above, such as the specific threshold levels and timings, are selected so that the above described triggering and cycling techniques perform effectively when implemented on an Esprit Ventilator across all possible lung parameters (resistance, compliance) for each patient type (adult, pediatric) and inherent variability and measurement uncertainties (noise, etc.). It is to be understood, however, that the present invention contemplates adaptively changing the algorithmic parameters of the present invention during the breathing cycle based on an estimation of desirable end points and optimization strategy to achieve a desired goal or goals. For example, triggering performance, e.g., thresholds, may be dynamically optimized based on minimizing the work of breathing required to trigger a breath on one hand and minimizing the ventilator autocycling (false triggering) on the other. Thus, for this example, the triggering criterion may be adjusted breath by breath using any conventional technique, such as dynamical programming, neural networks, fuzzy logic, etc., while signs of autocycling are being estimated or monitored. The adjustment of triggering criterion would change direction or weighting as the measure of autocycling approaches or exceeds a minimum threshold.

Autocyclying may be detected, for example, based on analysis of possible range of lung mechanics, rate and speed of change of pressure and flow measurements, delivered tidal volume versus exhaled volume, etc. One feasible method is to observe the rate of change of tidal volume for similar breath settings. For example, under pressure-controlled breath delivery, the faster the ventilator autocycles, the smaller the delivered tidal volume would become for consecutive breaths, because the patient does not get enough time to exhale and the same pressure level will be reached with a smaller inspiratory volume.

5. Leak Rate Error Correction and Display

It can be appreciated that in the ventilator system of the present invention, some situations may occur where the leak rate $Q_{leak}$ cannot be accurately determined. To account for these contingencies, the present invention implements a process for checking whether the leak rate determined during the current breathing cycle and/or processing cycle is valid, and for ensuring proper operation of the ventilator system even if the leak rate during a processing cycle is not valid. In particular, the following logic algorithm is implemented to reset or control the leak factor LF and the cycle threshold flow (CTF) when the actual leak rate is undetermined during a processing cycle.

According to this process, during each processing cycle, a check is made to determine if the leak rate determined for that cycle is valid. With a constant bias flow in the ventilation system, the leak rate is deemed invalid if the exhaust flow $Q_{exhaust}$ is significantly less than the bias flow. This can occur, for example, if the patient interface device becomes dislodged so that little flow is being exhausted through exhaust assembly 56. In a preferred embodiment of the present invention, the current leak rate $Q_{leak}(n)$ is also deemed invalid if (1) the exhaust flow $Q_{exhaust}$ is less than 1 LPM during the expiratory phase of the breathing cycle, or (2) a worst case estimated compliance factor exceeds extreme thresholds. In a preferred embodiment of the present invention, the first condition is not checked during the first 200 ms restricted segment of the exhalation phase.

The worst case estimated compliance factor ($C_{WC}$) is computed as follows. During each inhalation phase, a worst case total gas volume (WCTV) delivered to the patient is computed assuming extreme leak rates ($Q_{leak,\ max}$) of 80 liters per minute (lpm) for pediatrics and 100 lpm for adults. This first involves comparing the flow of gasses delivered to the patient $Q_{delivered}$ with the extreme leak rate $Q_{leak,\ max}$ during each processing cycle (n) to determine a difference $\Delta Q(n)$ therebetween. In other words, $\Delta Q(n)$ is determined during each processing cycle (n) as follows:

$$\Delta Q(n) = Q(n)_{delivered} - Q_{leak,\ max}, \quad (15)$$

where $Q(n)_{delivered}$ corresponds to the sum of all of the flows of gas delivered to the patient, i.e., $Q(n)_{delivered} = Q_{primary} + Q_{secondary}$. If the delivered flow $Q_{delivered}$ is less than $Q_{leak,\ max}$, then $\Delta Q(n)$ is set to zero. The worst case total gas volume WCTV is then determined over the inhalation cycle by summing the differences $\Delta Q(n)$ between $Q_{delivered}$ and $Q_{leak,\ max}$ determined during each processing cycle over the inhalation period. That is, WCTV is determined as:

$$WCTV = 0.005 * \sum_{n=0}^{n=N} \Delta Q(n), \quad (16)$$

where n is a processing cycle, i.e., a 5 ms time interval, and N is the total number of processing cycles in the inhalation period of the breathing cycle.

The worst case estimated compliance factor $C_{WC}$ is then determined as:

$$C_{WC} = WCTV/PIP, \quad (17)$$

wherein PIP=peak inspiratory pressure. At the end of every inhalation, if $C_{WC}$ is greater than 150 ml/cmH$_2$O for pediatrics, or 300 ml/cmH$_2$O for adults, then the leak rate estimate is considered invalid. It is to be understood that the threshold against which $C_{WC}$ is compared can be values other than 150 ml/cmH$_2$O for pediatrics or 300 ml/cmH$_2$O for adults and the present invention is not intended to be limited to these particular values.

A first flag (Leak Flag 1) and a second flag (Leak Flag 2) are initially set to true. Thereafter, the value of these flags is altered as set forth below, to control the leak factor LF and the cycle threshold flow (CTF) depending on the values of these flags. If, during a processing cycle, the above condition for an invalid leak rate is met, the two flags are both set to false, i.e., Leak Flag 1=false, and Leak Flag 2=false, meaning that the current leak rate determination should not be used by the processor. If, on the other hand, the above condition for an invalid leak is not met, i.e., the leak rate is valid, Leak Flag 1 is set to true. Note that Leak Flag 2 is not necessarily set to true at this time.

The ventilator system then determines if the patient is in the exhalation phase. If so, and if the second flag (Leak Flag 2) is false and the first flag (Leak Flag 1) is true, then the patient is considered to be in the non-active exhalation segment for triggering purposes, and the leak factor is set to zero. This allows the ventilator to properly trigger even though the leak rate has not been valid for an entire breath cycle. If the patient is in the exhalation phase and the second flag (Leak Flag 2) is true, the leak rate error process continues, and the second flag (Leak Flag 2) is not reset to at this time.

If the patient is in the inhalation phase, and the first and second flags are false, then the CTF is set to 45% of the peak flow and the leak factor is set to zero. Furthermore, if the leak rate is determined to be invalid, the bias flow reference is set to 20 lpm for adults and to 10 lpm for a pediatric patient. If the above conditions for an invalid leak are not met, i.e., the leak rate is valid, the first flag (Leak Flag 1) is set to true and the second flag is also set to true. Because the second flag is only reset to true during the inspiratory phase of the breathing cycle, it effectively forces the ventilator system to collect one whole breathing cycle worth of valid leak rate data before the ventilator system will use that leak flow data.

In an exemplary preferred embodiment of the present invention, the estimated leak flow $Q_{leak}$ is displayed for each breath. If the estimated leak flow exceeds an alarm threshold, a high leak alarm is generated. This high leak alarm is preferably selectively set by the operator.

The invention has been described above as being implemented in a digital processor running at a certain operating speed. It is be understood, that this operating speed can be varied. In which case, it may be necessary to change certain constants used in the above calculations. In addition, it is to be understood that the present invention need not be implemented in a digital processor. On the contrary, the entire system, or components of the system can be implemented in analog (continuous) form rather than in the digital (discrete) from discussed herein. Of course, implementing all or parts of the system in an analog system may require appropriate modification to the techniques discussed above.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims

What is claimed is:

1. A system for providing a flow of gas to a patient comprising:
    a pressure generating system adapted to provide a flow of gas responsive to a control signal;
    a patient circuit having a first end coupled to the pressure generating system and adapted to communicate the flow of gas with an airway of a patient;
    a flow sensor adapted to measure the flow of gas in the patient circuit and to output a first flow signal indicative thereof;
    a pressure sensor adapted to measure a pressure of the flow of gas in the patient circuit and to output a first pressure signal indicative thereof;
    an exhaust assembly adapted to communicate gas from within the patient circuit to ambient atmosphere; and
    a controller that receives the first flow signal and the first pressure signal and outputs the control signal that controls the flow of gas delivered to the patient circuit by the pressure generating system and, hence, the flow of gas at a patient's airway, wherein the controller detects onset of an inspiratory phase of a patient's breathing cycle for triggering an inspiratory flow of gas based on such a patient's inspiratory effort, which is determined based on both a flow related parameter determined from the first flow signal and a pressure related parameter determined from the first pressure signal.

2. The system according to claim 1, wherein the pressure generating system includes:
    a blower that receives a supply of gas from a gas source and provides the flow of gas;
    a flow controller associated with the blower to control a rate of the flow of gas responsive to the control signal.

3. The system according to claim 1, wherein the flow sensor is disposed in the first end of the patient circuit.

4. The system according to claim 1, wherein the patient circuit is a two-limb circuit.

5. The system according to claim 1, wherein the exhaust assembly includes an exhaust flow controller to control a rate of the exhaust flow of gas from the patient circuit responsive to an exhaust flow control signal provided by the controller.

6. The system according to claim 1, further comprising a secondary gas flow system that delivers a secondary flow of gas to the patient circuit, wherein the secondary gas flow system includes:
    a conduit configured and arranged so as to communicate the secondary flow of gas from a source of the secondary flow of gas to the patient circuit; and
    a second flow sensor adapted to measure the secondary flow of gas in the conduit and to output a second flow signal indicative thereof.

7. The system according to claim 1, wherein the controller establishes a trigger lockout interval, which is a period of time during each expiratory phase of a breathing cycle in which triggering the inspiratory flow of gas is prevented, based on at least one of the first flow signal and the first pressure signal.

8. The system according to claim 1, wherein the controller:
    determines a patient flow difference ($Q_{patient}-Q_{ref}$) as the flow related parameter, where $Q_{patient}$ is a current patient flow from the first flow signal and $Q_{ref}$ is a reference patient flow determined from the first flow signal at a start of a trigger window, which is a period of time during which triggering the inspiratory flow of gas is permitted;
    determines a patient pressure difference($P_{ref}-P_{patient}$) as the pressure related parameter, where $P_{patient}$ is a current patient pressure from the first pressure signal and $P_{ref}$ is a reference patient pressure determined from the first pressure signal at the start of the trigger window;
    determines the patient's inspiratory effort as a product of the patient flow difference and the patient pressure difference; and
    triggers the inspiratory flow of gas responsive to the patient's inspiratory effort exceeding a threshold.

9. The system according to claim 1, wherein the controller:
    determines a patient flow difference ($Q_{patient}-Q_{ref}$) as the flow related parameter, where $Q_{patient}$ is a current patient flow from the first flow signal and $Q_{ref}$ is a reference patient flow determined from the first flow signal at a start of a trigger window, which is a period of time during which triggering the inspiratory flow of gas is permitted;
    determines a patient pressure difference ($P_{ref}-P_{patient}$) as the pressure related parameter, where $P_{patient}$ is a current patient pressure from the first pressure signal and $P_{ref}$ is a reference patient pressure determined from the first pressure signal at the start of the trigger window;
    determines the patient's inspiratory effort as a product of the patient flow difference and the patient pressure difference;
    sums the patient's inspiratory efforts accumulated over a time interval; and
    triggers the inspiratory flow of gas responsive to the sum of the patient's inspiratory efforts over the time interval exceeding a threshold.

10. The system according to claim 1, wherein the controller:
    determines a patient pressure difference ($P_{ref}-P_{patient}$) as the pressure related parameter, where $P_{patient}$ is a current patient pressure from the first pressure signal and $P_{ref}$ is a reference patient pressure determined from the first pressure signal at a start of a trigger window;
    delays the patient pressure difference in time to determine a delayed patient pressure difference;
    determining a current patient flow from the first flow signal as the flow related parameter;

determines a product of a current patient flow and the delayed patient pressure difference as the patient's inspiratory effort;

sums the patient's inspiratory efforts accumulated over a time interval; and triggers the inspiratory flow of gas responsive to the sum of the patient's inspiratory effort exceeding a threshold.

11. The system according to claim 1, wherein the controller detects onset of an expiratory phase of a patient's breathing cycle for cycling from providing the inspiratory flow of gas to allowing an expiratory flow of gas from the exhaust assembly based on such a patient's expiratory effort, which is determined based on both the first flow signal and the first pressure signal.

12. The system according to claim 11, wherein the controller:

determines a patient flow difference ($Q_{ref}-Q_{patient}$), where $Q_{patient}$ is a current patient flow from the first flow signal and $Q_{ref}$ is a reference patient flow determined from the first flow signal at a start of a cycling window, which is a period of time during which the expiratory flow of gas from the patient circuit is permitted;

determines a patient pressure difference ($P_{patient}-P_{ref}$), where $P_{patient}$ is a current patient pressure from the first pressure signal and $P_{ref}$ is a reference patient pressure determined from the first pressure signal at the start of the cycling window;

determines the patient's expiratory effort as a product of the patient flow difference and the patient pressure difference; and cycles from providing the inspiratory flow of gas to allowing an expiratory flow of gas from the exhaust assembly responsive to the patient's expiratory effort exceeding a threshold.

13. The system according to claim 1, wherein the controller:

determines a patient pressure difference ($P_{patient}-P_{ref}$), where $P_{patient}$ is a current patient pressure from the first pressure signal and $P_{ref}$ is a reference patient pressure determined from the first pressure signal at a start of a cycling window, which is a period of time during which the expiratory flow of gas from the patient circuit is permitted;

delays a patient flow from the first flow signal to determine a delayed patient flow;

determines a product of the patient pressure difference and the delayed patient flow as the patient's expiratory effort;

sums the patient's expiratory efforts accumulated over a time interval; and cycles from providing the inspiratory flow of gas to allowing an expiratory flow of gas from the exhaust assembly responsive to the sum of the patient's expiratory effort exceeding a threshold.

14. The system according to claim 11, wherein the controller:

determines a patient flow difference ($Q_{ref}-Q_{patient}$), where $Q_{patient}$ is a current patient flow from the first flow signal and $Q_{ref}$ is a reference patient flow determined from the first flow signal at a start of a cycling window, which is a period of time during which the expiratory flow of gas from the patient circuit is permitted;

determines a patient pressure difference ($P_{patient}-P_{ref}$), where $P_{patient}$ is a current patient pressure from the first pressure signal and $P_{ref}$ is a reference patient pressure determined from the first pressure signal at the start of the cycling window;

determines the patient's expiratory effort as a product of the patient flow difference and the patient pressure difference;

sums the patient's expiratory efforts accumulated over a time interval; and cycles from providing the inspiratory flow of gas to allowing an expiratory flow of gas from the exhaust assembly responsive to the sum of the patient's expiratory efforts over the time interval exceeding a threshold.

15. The system according to claim 1, wherein the controller cycles from providing the inspiratory flow of gas to allowing an expiratory flow of gas from the exhaust assembly by comparing patient flow determined from the first flow signal against a cycle threshold flow and cycles responsive to the patient flow falling below the cycle threshold flow.

16. The system according to claim 15, wherein the controller:

monitors patient pressure, via the first pressure signal, at an end portion of an inspiratory phase and monitors patient flow, via the first flow signal, at a beginning portion of an expiratory phase to determine whether the system cycled too early or too late; and adjusts the cycle threshold flow for a next breathing cycle responsive to a determination that the system cycled too early or too late.

17. A method of providing a flow of gas to a patient comprising:

generating a flow of gas;

providing the flow of gas to a patient via a patient circuit;

controlling the flow of gas delivered to a patient responsive to a control signal;

measuring the flow of gas in the patient circuit and outputting a first flow signal indicative thereof;

measuring a pressure of the flow of gas in the patient circuit and outputting a first pressure signal indicative thereof;

communicating gas from within the patient circuit to ambient atmosphere; and detecting onset of an inspiratory phase of a patient's breathing cycle for triggering an inspiratory flow of gas based on such a patient's inspiratory effort, which is determined based on both a flow related parameter determined from the first flow signal and a pressure related parameter determined from the first pressure signal.

18. The method according to claim 17, wherein detecting the onset of the inspiratory phase includes:

determining a patient flow difference ($Q_{patient}-Q_{ref}$) as the flow related parameter, where $Q_{patient}$ is a current patient flow from the first flow signal and $Q_{ref}$ is a reference patient flow determined from the first flow signal at a start of a trigger window, which is a period of time during which the expiratory flow of gas is permitted;

determining a patient pressure difference ($P_{ref}-P_{patient}$) as the pressure related parameter, where $P_{patient}$ is a current patient pressure from the first pressure signal and $P_{ref}$ is a reference patient pressure determined from the first pressure signal at the start of the trigger window; and determining the patient's inspiratory effort as a product of the patient flow difference and the pressure difference.

19. The method according to claim 18, further comprising triggering an inspiratory flow of gas responsive to the patient's inspiratory effort exceeding a threshold.

20. The method according to claim 17, wherein detecting the onset of the inspiratory phase includes:
   determining a patient flow difference ($Q_{patient}-Q_{ref}$) as the flow related parameter, where $Q_{patient}$ is a current patient flow from the first flow signal and $Q_{ref}$ is a reference patient flow determined from the first flow signal at a start of a trigger window, which is a period of time during which the expiratory flow of gas is permitted;
   determining a patient pressure difference ($P_{ref}-P_{patient}$) as the pressure related parameter, where $P_{patient}$ is a current patient pressure from the first pressure signal and $P_{ref}$ is a reference patient pressure determined from the first pressure signal at a start of a trigger window;
   determining the patient's inspiratory effort as a product of a patient flow difference and the pressure difference;
   summing the patient's inspiratory efforts accumulated over a time interval; and
   triggering an inspiratory flow of gas responsive to the sum of the patient's inspiratory efforts over the time interval exceeding a threshold.

21. The method according to claim 17, wherein detecting the onset of the inspiratory phase includes:
   determining a patient pressure difference ($P_{ref}-P_{patient}$) as the pressure related parameter, where $P_{patient}$ is a current patient pressure from the first pressure signal and $P_{ref}$ is a reference patient pressure determined from the first pressure signal at a start of a trigger window, which is a period of time during which the expiratory flow of gas is permitted;
   determining a delayed patient pressure difference, where a length of the delay is selected so as to account for an inherent physiological delay between an onset of a pressure drop and a rise in patient flow occurring at a beginning of inspiration;
   determining a current patient flow from the first flow signal as the flow related parameter;
   determining a product of the current patient flow and the delayed patient pressure difference as the patient's inspiratory effort;
   summing the patient's inspiratory efforts accumulated over a time interval; and
   triggering an inspiratory flow of gas responsive to the sum of the patient's inspiratory effort exceeding a threshold.

22. The method according to claim 17, further comprising detecting onset of an expiratory phase of a patient's breathing cycle for cycling from providing an inspiratory flow of gas to allowing an expiratory flow of gas from the patient circuit based on such a patient's expiratory effort, wherein detecting the onset of an expiratory phase is determined based on both the first flow signal and the first pressure signal.

23. The method according to claim 22, wherein detecting an onset of an expiratory phase includes:
   determining a patient flow difference ($Q_{ref}-Q_{patient}$), where $Q_{patient}$ is a current patient flow from the first flow signal and $Q_{ref}$ is a reference patient flow determined from the first flow signal at a start of a cycling window, which is a period of time during which the expiratory flow of gas from the patient circuit is permitted;
   determining a patient pressure difference ($P_{patient}-P_{ref}$), where $P_{patient}$ is a current patient pressure from the first pressure signal and $P_{ref}$ is a reference patient pressure determined from the first pressure signal at the start of the cycling window;
   determining the patient's expiratory effort as a product of the patient flow difference and the patient pressure difference; and
   cycling from providing an inspiratory flow of gas to allowing an expiratory flow of gas from th patient circuit responsive to the patient's expiratory effort exceeding a threshold.

24. The method according to claim 22, wherein detecting an onset of an expiratory phase includes:
   determining a patient pressure difference ($P_{patient}-P_{ref}$), where $P_{patient}$ is a current patient pressure from the first pressure signal and $P_{ref}$ is a reference patient pressure determined from the first pressure signal at a start of a cycling window, which is a period of time during which the expiratory flow of gas from the patient circuit is permitted;
   delaying a patient flow from the first flow signal to determine a delayed patient flow;
   determining a product of the patient pressure difference and the delayed patient flow as the patient's expiratory effort;
   summing the patient's expiratory efforts accumulated over a time interval; and
   cycling from providing an inspiratory flow of gas to allowing an expiratory flow of gas from the patient circuit responsive to the sum of the patient's expiratory effort exceeding a threshold.

25. The method according to claim 22, wherein detecting an onset of an expiratory phase includes:
   determining a patient flow difference ($Q_{ref}-Q_{patient}$), where $Q_{patient}$ is a current patient flow from the first flow signal and $Q_{ref}$ is a reference patient flow determined from the first flow signal at a start of a cycling window, which is a period of time during which the expiratory flow of gas from the patient circuit is permitted;
   determining a patient pressure difference ($P_{patient}-P_{ref}$), where $P_{patient}$ is a current patient pressure from the first pressure signal and $P_{ref}$ is a reference patient pressure determined from the first pressure signal at the start of the cycling window;
   determining the patient's expiratory effort as a product of the patient flow difference and the patient pressure difference;
   summing the patient's expiratory efforts accumulated over a time interval; and
   cycling from providing an inspiratory flow of gas to allowing an expiratory flow of gas from the patient circuit responsive to the sum of the patient's expiratory efforts over the time interval exceeding a threshold.

26. The method according to claim 17, wherein the controller cycles from providing an inspiratory flow of gas to allowing an expiratory flow of gas from the patient circuit by comparing patient flow determined from the first flow signal against a cycle threshold flow and cycles responsive to the patient flow falling below the cycle threshold flow.

27. The method according to claim 26, further comprising:
- monitoring patient pressure, via the first pressure signal, at an end portion of an inspiratory phase;
- monitoring patient flow, via the first flow signal, at a beginning portion of an expiratory phase;
- determining whether cycling occurred too late based on the patient pressure at the end portion of the inspiratory phase;
- determining whether cycling occurred too early based on the patient flow at the beginning portion of the expiratory phase; and
- adjusting the cycle threshold flow for a next breathing cycle responsive to a determination that cycling occurred too early or too late.

* * * * *

US006823866C1

(12) EX PARTE REEXAMINATION CERTIFICATE (9244th)
United States Patent
Jafari et al.

(10) Number: US 6,823,866 C1
(45) Certificate Issued: Aug. 28, 2012

(54) MEDICAL VENTILATOR TRIGGERING AND CYCLING METHOD AND MECHANISM

(75) Inventors: Mehdi M. Jafari, Laguna Hills, CA (US); Gardner J. Kimm, Carlsbad, CA (US); Karrie McGuigan, San Marcos, CA (US)

(73) Assignee: RIC Investments, LLC, Wilmington, DE (US)

Reexamination Request:
No. 90/011,363, Nov. 30, 2010

Reexamination Certificate for:
Patent No.: 6,823,866
Issued: Nov. 30, 2004
Appl. No.: 10/617,590
Filed: Jul. 11, 2003

Related U.S. Application Data

(63) Continuation of application No. 09/970,383, filed on Oct. 2, 2001, now Pat. No. 6,626,175.
(60) Provisional application No. 60/238,387, filed on Oct. 6, 2000.

(51) Int. Cl.
*A61M 16/00* (2006.01)
*A61M 16/10* (2006.01)
*A61M 16/20* (2006.01)
*A61M 16/12* (2006.01)

(52) U.S. Cl. .............................. 128/204.21; 128/204.18
(58) Field of Classification Search .............. 128/204.21
See application file for complete search history.

(56) References Cited

To view the complete listing of prior art documents cited during the proceeding for Reexamination Control Number 90/011,363, please refer to the USPTO's public Patent Application Information Retrieval (PAIR) system under the Display References tab.

*Primary Examiner* — Aaron J. Lewis

(57) ABSTRACT

A medical ventilator system and method that triggers, cycles, or both based on patient effort, which is determined from cross-correlating patient flow and patient pressure. The medical ventilator is also controlled such that sensitivity to a patient initiated trigger increases as the expiratory phase of the breathing cycle progresses. The present invention also provides adaptive adjustment of cycling criteria to optimize the cycling operation.

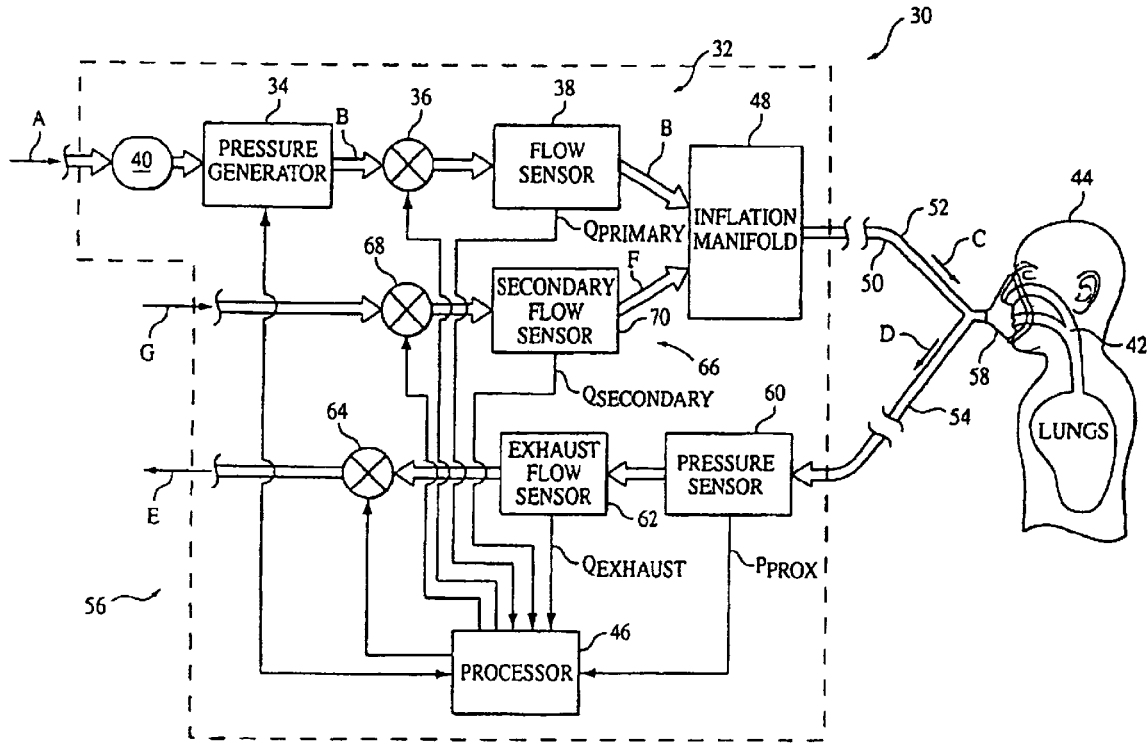

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-27 is confirmed.

New claims 28-37 are added and determined to be patentable.

*28. The system of claim 1, wherein the controller detecting the onset of the inspiratory phase of the patient's breathing cycle includes detecting, during a quiet exhalation segment, a decrease in the first pressure signal, followed by an increase in the first flow signal indicating an increase in the inspiratory flow of the gas at the patient's airway.*

*29. The system of claim 1, wherein the controller detecting the onset of the inspiratory phase of the patient's breathing cycle includes determining that an estimated patient effort is greater than a threshold, where the estimated patient effort is determined as a sum, over a time window during a quiet exhalation segment, of products: (1) a difference in the measured flow of the gas over the time window; and (2) a delayed difference in the measure pressure of the gas over the time window.*

*30. The system of claim 1, wherein the flow related parameter is a measured patient flow difference between a measured flow at a given time and a reference flow measured at a start of a time window, and wherein the pressure related parameter is a measured pressure difference between a measured pressure at a time earlier than the given time and a reference pressure measured at the start of the time window.*

*31. The system of claim 1, wherein the controller further detects onset of an expiratory phase of the patient's breathing cycle for cycling from the providing the inspiratory flow of gas to allowing an expiratory flow of gas from the exhaust assembly base on the patient's expiratory effort, including detecting a decrease in the first flow signal indicating a decrease in the inspiratory flow of the gas at the patient's airway followed by an increase in the first pressure signal.*

*32. The system of claim 1, wherein the controller further detects onset of an expiratory phase of the patient's breathing cycle for cycling from providing the inspiratory flow of gas to allowing an expiratory flow of gas from the exhaust assembly based on the patient's expiratory effort, including determining that an estimated patient effort is greater than a threshold, where the estimated patient effort is determined as a sum, over a time interval, of products of: (1) a difference in the measured pressure of the gas over the time interval; and (2) a delayed difference in the measured flow of the gas over the time interval.*

*33. The method of claim 17, wherein detecting the onset of the inspiratory phase of the patient's breathing cycle includes detecting, during a quiet exhalation segment, a decrease in the first pressure signal, followed by an increase in the first flow signal indicating an increase in the inspiratory flow of the gas at the patient's airway.*

*34. The method of claim 17, wherein detecting the onset of the inspiratory phase of the patient's breathing cycle includes determining that an estimated patient effort is greater than a threshold, where the estimated patient effort is determined as a sum, over a time window during a quiet exhalation segment, of products of: (1) a difference in the measured flow of the gas over the time window; and (2) a delayed difference in the measured pressure of the gas over the time window.*

*35. The method of claim 17, wherein the flow related parameter is a measured patient flow difference between a measured flow at a given time and a reference flow measured at a start of a time window, and wherein the pressure related parameter is a measured pressure difference between a measured pressure at a time earlier than the given time and a reference pressure measured at the start of the time window.*

*36. The method of claim17, further comprising detecting onset of an expiratory phase of the patient's breathing cycle for cycling from providing the inspiratory flow of gas to allowing an expiratory flow of gas from the exhaust assembly based on the patient's expiratory effort, including detecting a decrease in the first flow signal indicating a decrease in the inspiratory flow of the gas at the patient's airway followed by an increase in the first pressure signal.*

*37. The method of claim 17, further comprising detecting onset of an expiratory phase of the patient's breathing cycle for cycling from providing the inspiratory flow of gas allowing an expiratory flow of gas from the exhaust assembly based on the patient's expiratory effort, including determining that an estimated patient effort is greater than a threshold, where the estimated patient effort is determined as a sum, over a time interval, of products of: (1) difference in the measured pressure of the gas over the time interval; and (2) delayed difference in the measured flow of the gas over the time interval.*

\* \* \* \* \*